(12) United States Patent
Cragg et al.

(10) Patent No.: US 7,201,725 B1
(45) Date of Patent: Apr. 10, 2007

(54) DEVICE AND METHOD FOR DETERMINING A DEPTH OF AN INCISION

(75) Inventors: Andrew H. Cragg, San Clemente, CA (US); Rodney Brenneman, San Clemente, CA (US); Mark Ashby, San Clemente, CA (US); Eduardo Chi Sing, San Clemente, CA (US)

(73) Assignee: Sub-Q, Inc., San Clemente, CA (US)

( * ) Notice: Subject to any disclaimer, the term of this patent is extended or adjusted under 35 U.S.C. 154(b) by 159 days.

(21) Appl. No.: 10/069,107

(22) PCT Filed: Sep. 25, 2000

(86) PCT No.: PCT/US00/26367

§ 371 (c)(1), (2), (4) Date: Dec. 16, 2002

(87) PCT Pub. No.: WO01/21058

PCT Pub. Date: Mar. 29, 2001

(51) Int. Cl.
A61B 5/117 (2006.01)
A61B 5/103 (2006.01)

(52) U.S. Cl. .................................... 600/587

(58) Field of Classification Search ............... 600/587; 604/15, 57, 60, 73, 248, 256, 264, 506; 606/50, 606/191, 213–215, 174, 178, 180, 151, 194; 128/898
See application file for complete search history.

(56) References Cited

U.S. PATENT DOCUMENTS

| | | | |
|---|---|---|---|
| 581,235 A | 4/1897 | Kenyon |
| 1,578,517 A | 3/1926 | Hein |
| 2,086,580 A | 7/1937 | Shirley |
| 2,465,357 A | 3/1949 | Correll |
| 2,492,458 A | 12/1949 | Bering, Jr. |
| 2,507,244 A | 5/1950 | Correll |

(Continued)

FOREIGN PATENT DOCUMENTS

| | | |
|---|---|---|
| EP | 032826 A2 | 7/1981 |
| EP | 476178 A1 | 3/1992 |
| EP | 482350 A2 | 4/1992 |
| EP | 0557963 | 2/1993 |
| EP | 0637431 | 11/1994 |
| FR | 2 641 692 | 7/1990 |

(Continued)

OTHER PUBLICATIONS

J. Bryne Review Article: Endovascular treatments for intracranial anuerysms, 1996 The British journal of radiology; 98, 891-899.

(Continued)

Primary Examiner—Max F. Hindenburg
Assistant Examiner—Brian Szmal
(74) Attorney, Agent, or Firm—Miller Matthias & Hull

(57) ABSTRACT

A device for determining the depth of an incision from the epidermal layer to a puncture in a blood vessel in which the device includes an elongated member which has a lumen extending from a distal end to a proximal end. The distal end of the elongated member is configured to locate the blood vessel. After the device locates the blood vessel, a depth indicator is positioned to mark the depth of the blood vessel. In one embodiment, the elongated member includes a tapering interior surface which can receive a portion of the blood vessel. An extending control member may extend from the device at the distal end wherein the extending control member enters the blood vessel before the device locates the vessel. Fluid from the blood vessel enters the extending member through a vent hole and exits through an opening at the proximal end of the device, thereby providing a user with visual feedback that the device is moving in the desired direction toward the blood vessel.

41 Claims, 13 Drawing Sheets

U.S. PATENT DOCUMENTS

| | | |
|---|---|---|
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1958 | Thompson |
| 2,899,362 A | 8/1959 | Sieger, Jr. et al. |
| 3,157,524 A | 11/1964 | Artandi |
| 3,724,465 A | 4/1973 | Duchane |
| 4,000,741 A | 1/1977 | Binard et al. |
| 4,211,323 A | 7/1980 | Olsen |
| 4,218,155 A | 8/1980 | Weidner |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zuloowski |
| 4,404,970 A | 9/1983 | Sawyer |
| 4,515,637 A | 5/1985 | Cioca |
| 4,573,576 A | 3/1986 | Krol |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,645,488 A | 2/1987 | Matukas |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,163,904 A | 11/1992 | Lampropoulos et al. |
| 5,167,624 A | 12/1992 | Butler et al. |
| 5,192,300 A | 3/1993 | Fowler |
| 5,192,301 A | 3/1993 | Kamiya et al. |
| 5,195,988 A | 3/1993 | Haaga |
| 5,220,926 A | 6/1993 | Jones |
| 5,221,259 A | 6/1993 | Weldon et al. |
| 5,242,683 A | 9/1993 | Klaveness |
| 5,275,616 A | 1/1994 | Fowler |
| 5,282,827 A | 2/1994 | Kensey et al. |
| 5,310,407 A | 5/1994 | Casale |
| 5,322,515 A | 6/1994 | Karas et al. |
| 5,325,857 A | 7/1994 | Nabai et al. |
| 5,334,216 A | 8/1994 | Vidal et al. |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammerslag |
| 5,385,550 A | 1/1995 | Su et al. |
| 5,388,588 A | 2/1995 | Nabai et al. |
| 5,391,183 A | 2/1995 | Janzen et al. |
| 5,395,353 A * | 3/1995 | Scribner ............ 604/264 |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A * | 8/1995 | Janzen ............ 604/506 |
| 5,443,481 A | 8/1995 | Lee |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers et al. |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammerslag |
| 5,540,715 A | 7/1996 | Katsaros et al. |
| 5,542,914 A | 8/1996 | Van Iten |
| 5,545,178 A | 8/1996 | Kensey et al. |
| 5,558,853 A | 9/1996 | Quay |
| 5,591,204 A | 1/1997 | Janzen et al. |
| 5,591,205 A | 1/1997 | Fowler |
| 5,601,602 A * | 2/1997 | Fowler ............ 606/213 |
| 5,601,603 A | 2/1997 | Illi |
| 5,645,566 A * | 7/1997 | Brenneman et al. ........ 606/213 |
| 5,649,547 A | 7/1997 | Ritchart et al. |
| 5,653,730 A | 8/1997 | Hammerslag |
| 5,665,107 A | 9/1997 | Hammerslag |
| 5,676,689 A | 10/1997 | Kensey et al. |
| 5,681,279 A | 10/1997 | Roper et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,063,085 A * | 5/2000 | Tay et al. ............ 606/50 |
| 6,071,300 A | 6/2000 | Brenneman et al. |
| 6,071,301 A | 6/2000 | Cragg et al. |
| 6,086,607 A | 7/2000 | Cragg et al. |
| 6,161,034 A | 12/2000 | Burbank et al. |
| 6,162,192 A * | 12/2000 | Cragg et al. ............ 604/15 |
| 6,183,497 B1 | 2/2001 | Sing et al. |
| 6,200,328 B1 | 3/2001 | Cragg et al. |
| 6,315,753 B1 * | 11/2001 | Cragg et al. ............ 604/15 |

FOREIGN PATENT DOCUMENTS

| | | |
|---|---|---|
| GB | 1509023 | 4/1978 |
| GB | 1569660 | 6/1980 |
| RU | 782814 | 11/1980 |
| RU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 98/06346 | 2/1998 |
| WO | WO 99/66834 | 12/1999 |

OTHER PUBLICATIONS

John T. Correll, et al., A new Physiologically absorbable sponge.

John T. Correll, et al. Biologic investigations of new absorbable sponge; p. 585.

Fandrich, C., et al. "Small guage gelfoam plug liver biopsy in high risk patients", Australian Radiology, vol. 40, pp. 230-234 (1996).

Journal of interventional cardiology vol. 5 No. 2 Jun.

Kassell, et al., Size of Intracanial aneurysm; vol. 12, No. 3, (1983).

Schievink, et al. The new england journal of medicaine; review articles; intracanial aneurysms; Jan. 2, 1997.

Szikora, et al. Combined Use of stents and cells to treat experimental wide-necked carotid anueryms: Preliminary results; AJNR AM newradiol 15: 1091-1102, Jun. 94.

Szikora, et al. Endovascular treatment of experimental anuerysms with liquid polymers: vol. 38, No. 2, Feb. 96.

Turjman, et al. Combined stent implantation & endosacular coil placement for tretment of experimental wide-necked aneurysms:AJNRAM J. Neuroradio 15: 1087-1090 Jun. 94.

Yoshimoto, et al cerebral anuerysms unrelated to arterial bifurcations; Acta neurochir (Wien) (96) 138:958-964.

David J. Allison, M.D., et al., "Percutaneous Liver Biopsy and Track Embolization with Steel Coils," *Radiology*, 169(1):261-263 (1988).

Vincent P. Chueng, M.D., et al., "Sheath Needle for Liver Biopsy in High-Risk Patients," *Radiology*, 166:261-262 (1988).

J.P.M. Foran, et al., "*Early Mobilisation After Percutaneous Cardiac Catheterisation Using Collagen Plug (VasoSeal) Haemostasis*," Br Heart, vol. 69 (1993) pp. 424-429.

JSR Gibbs, "*Fermoral Arterial Hemostasis*," Journal of Interventional Cardiology, v 5 (1992) pp. 85-88.

Ferdinand Kiemeneij, MD, et al., "Improved Anticoagulation Management After Palmaz Schatz Coronary Stent Implantation by Sealing the Arterial Puncture Site With a Vascular Hemostasis Device," *Catheterization and Cardiovascular Diagnosis*, 30:317-322 (1993).

W.G. Kussmaul, "*Rapid Arterial Hemostasis*," Journal of the American College of Cardiology, vol. 25 (1995) pp. 1685-1692.

Pharmacia & Upjohn Manufacturer Brochure, "*Gelfoam Sterile Sponge, Sterile Powder, and Sterile Film*,"(May 1997): pp. 1-34.

Pharmacia & Upjohn Manufacturer Brochure, "*Gelfoam Sterile Powder*," (Feb. 1996).

Pharmacia & Upjohn Manufacturer Brochure, "*Gelfoam Sterile Powder*," (Mar. 1996).

Pharmacia & Upjohn Manufacturer Specification, "*Gelfoam Sterile Sponge, Sterile Powder and Sterile Film*" (Nov. 1996): pp. 1-23.

Pharmacia & Upjohn Manufacturer Brochure for Gelfoam, 1996.

S.A. Riley, et al., "Percutaneous Liver Biopsy with Plugging of Needle Track: A Safe Method for Use in Patients with Impaired Coagulation," *The Lancet*, p. 436 (1984).

Timothy A. Sanborn, MD, et al., "*Multicenter Randomized Trial Comparing a Percutaneous Collagen Hemostasis Device With Conventional Manual Compression After Diagnostic Angiography and Angioplasty*," Journal of American College of Cardiology, vol. 22, No. 5 (1993) pp. 1273-1279.

Schrader, R., "*Collagen Application*," Catheterization and Cardiovascular Diagnosis, (1992) pp. 298-302.

Sigmund Silber, M.D., FACC, "Rapid Hemostasis of Arterial Puncture Sites with Collagen in Patients Undergoing Diagnostic and Interventional Cardiac Catheterization," *Clinical Cardiology*, 20:981-992 (1997).

Tony P. Smith, M.D., et al., "Percutaneous Transhepatic Liver Biopsy with Tract Embolization," *Radiology*, 198:769-774 (1996).

Marc Zins, M.D., et al., "US-guided Percutaneous Liver Biopsy with Plugging of the Needle Track: A Prospective Study in 72 High-Risk Patients," *Radiology*, 184(3):841-843 (1992).

* cited by examiner

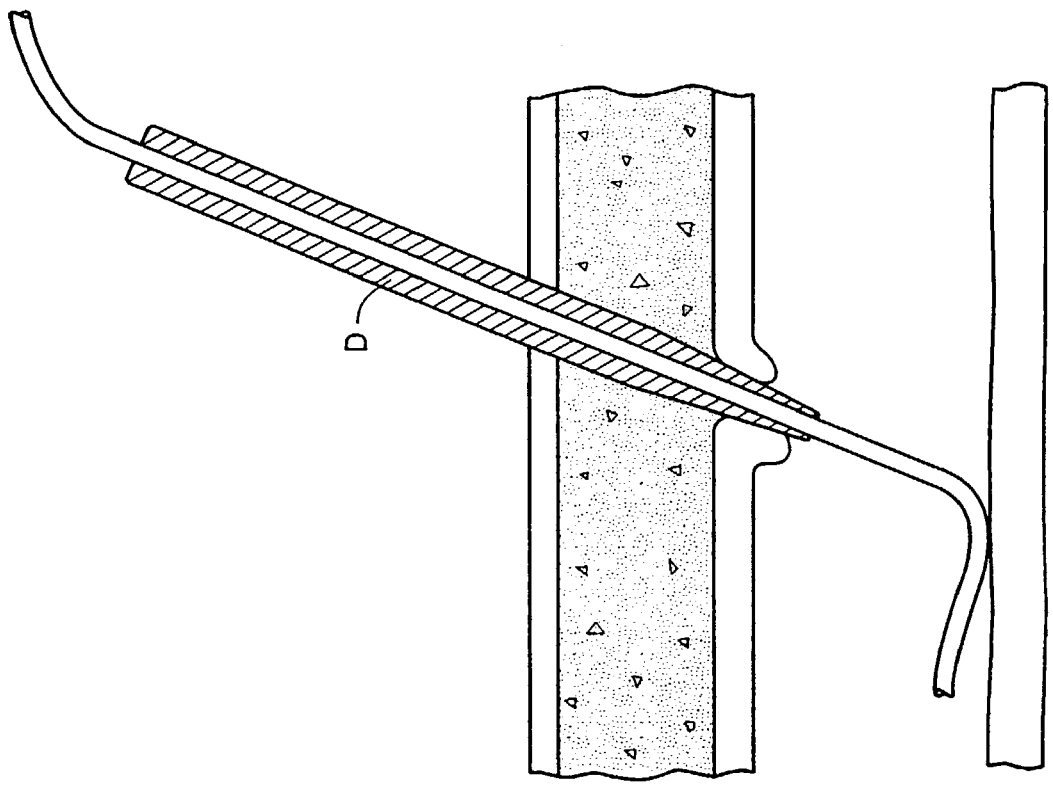
FIG._2 (PRIOR ART)
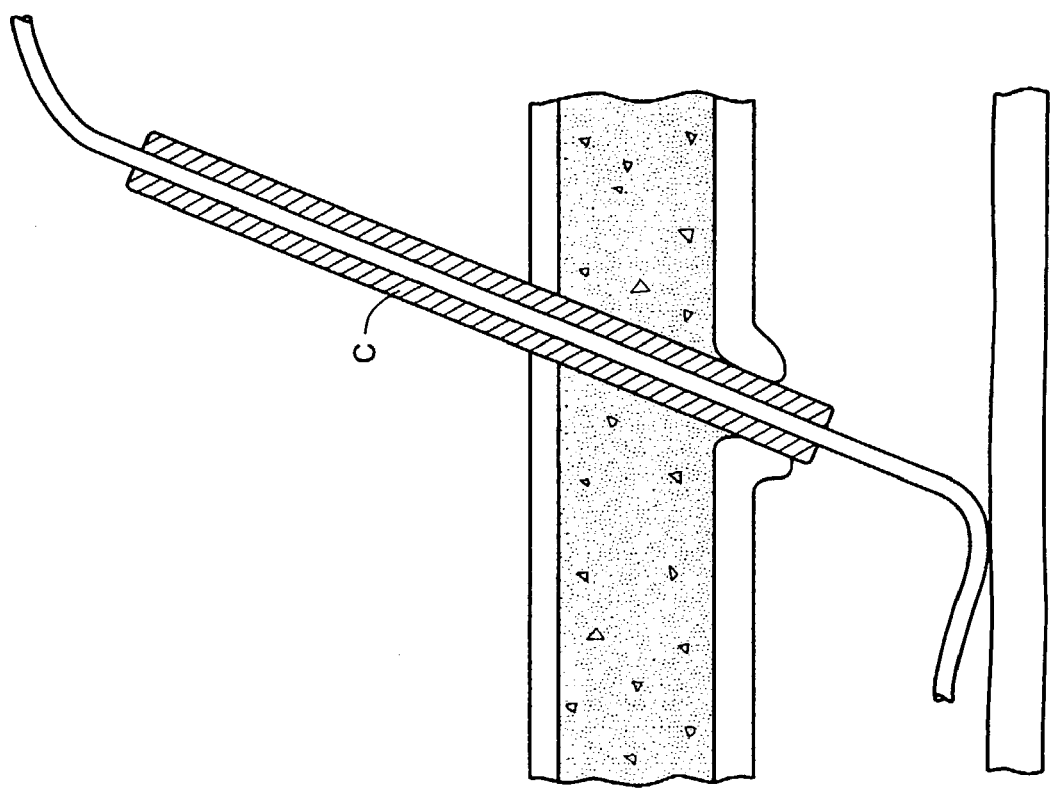
FIG._1 (PRIOR ART)

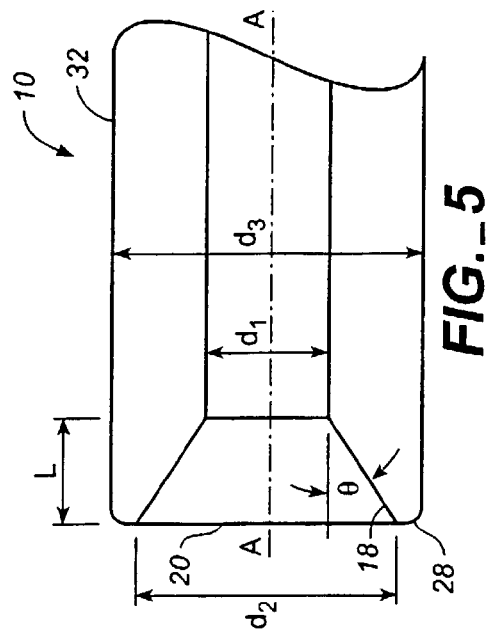
FIG._5
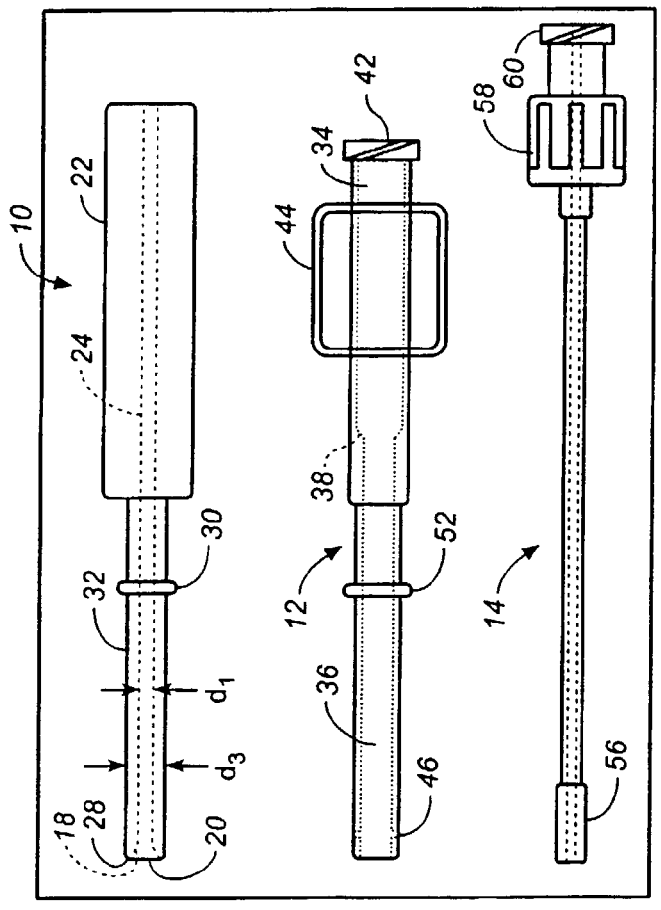
FIG._3
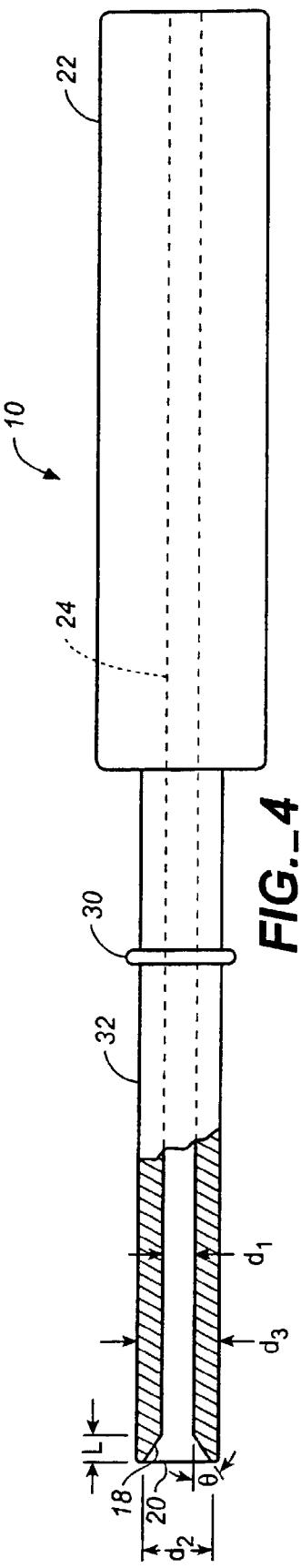
FIG._4

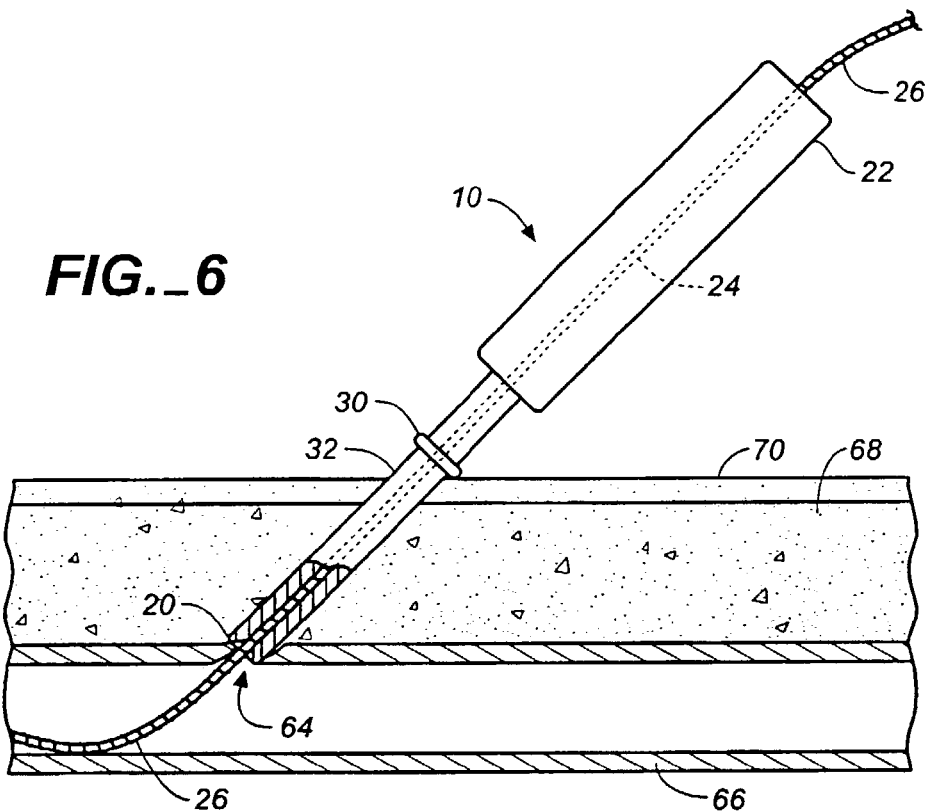
FIG._6
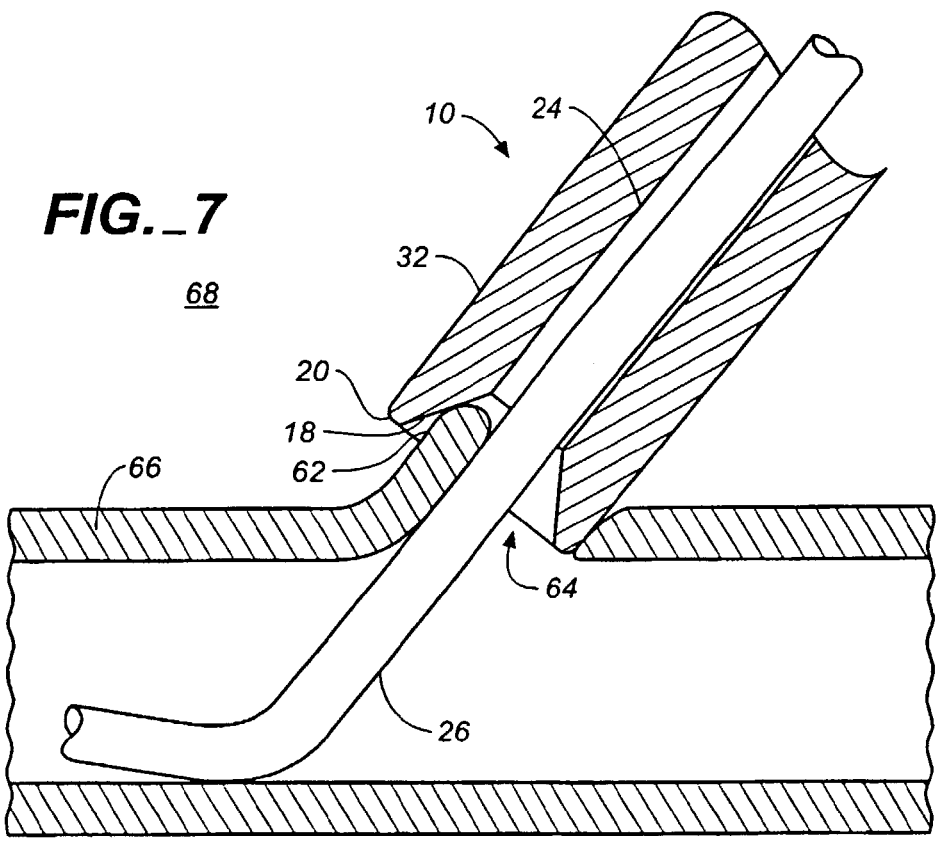
FIG._7

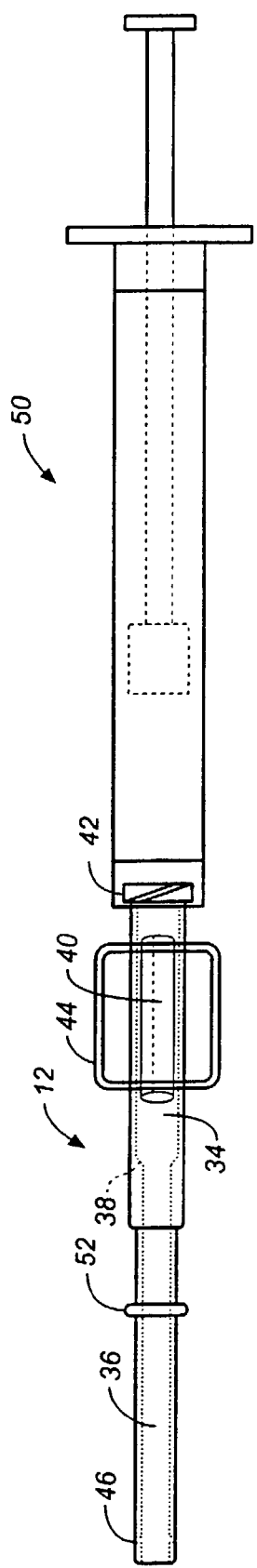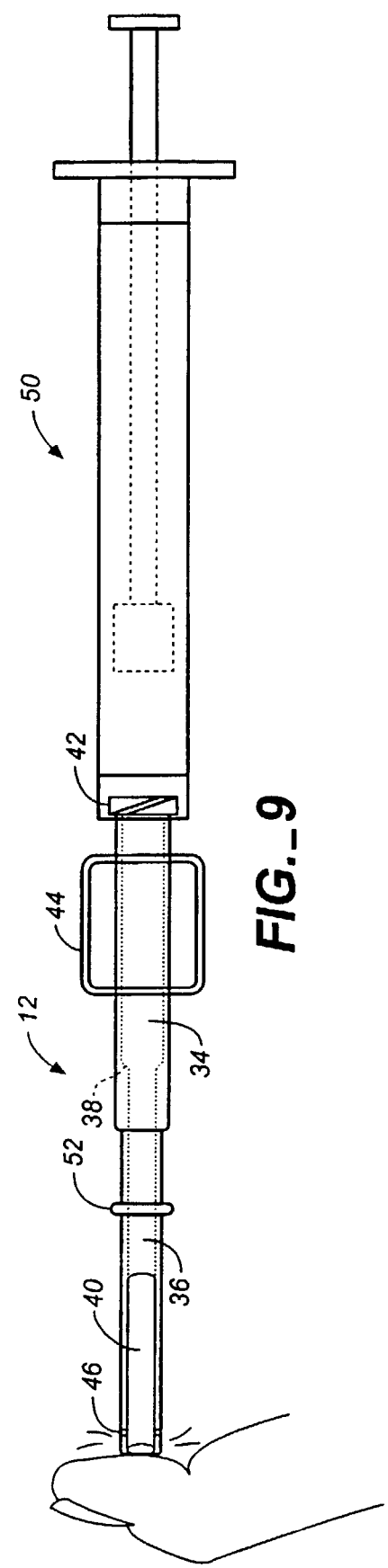

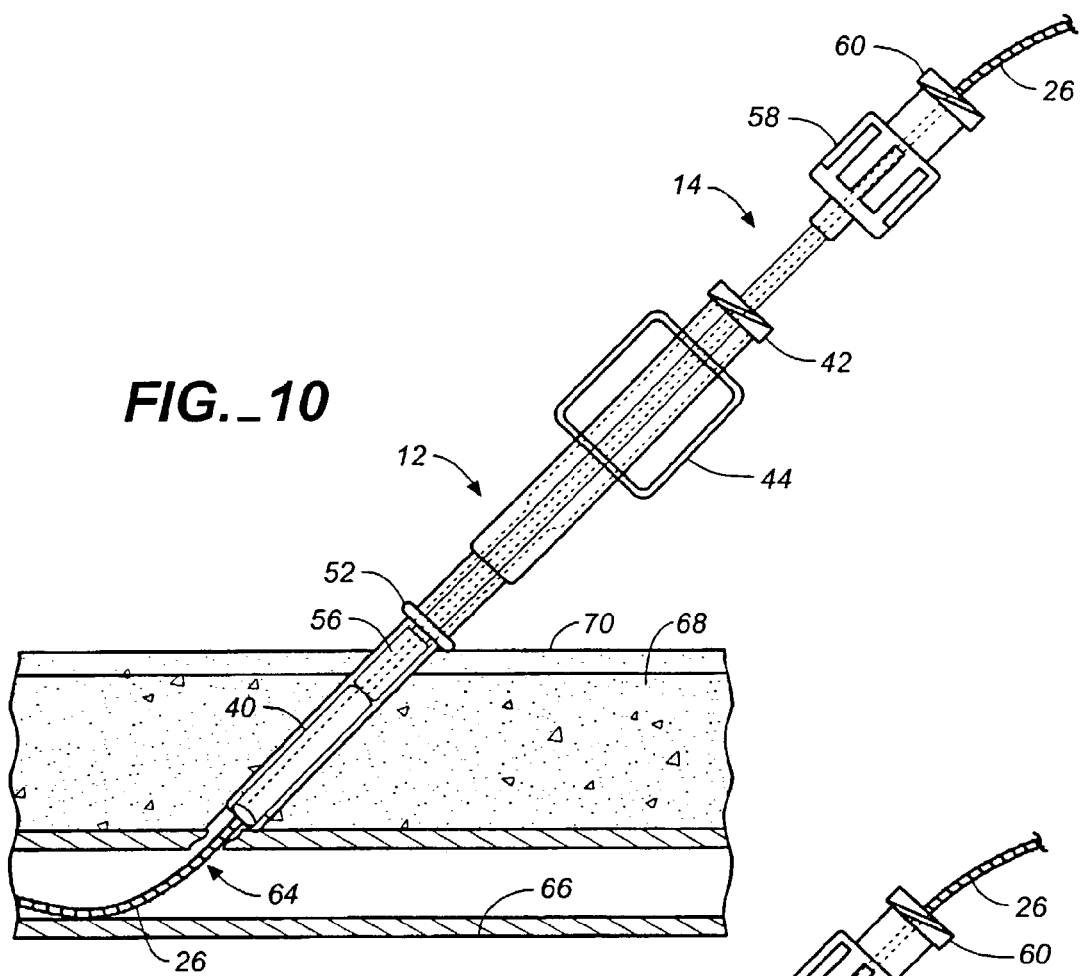
FIG._10
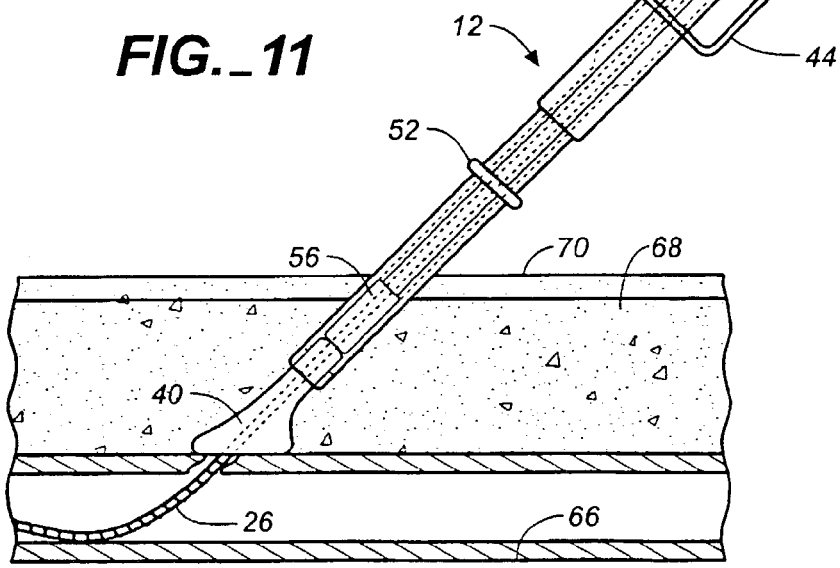
FIG._11

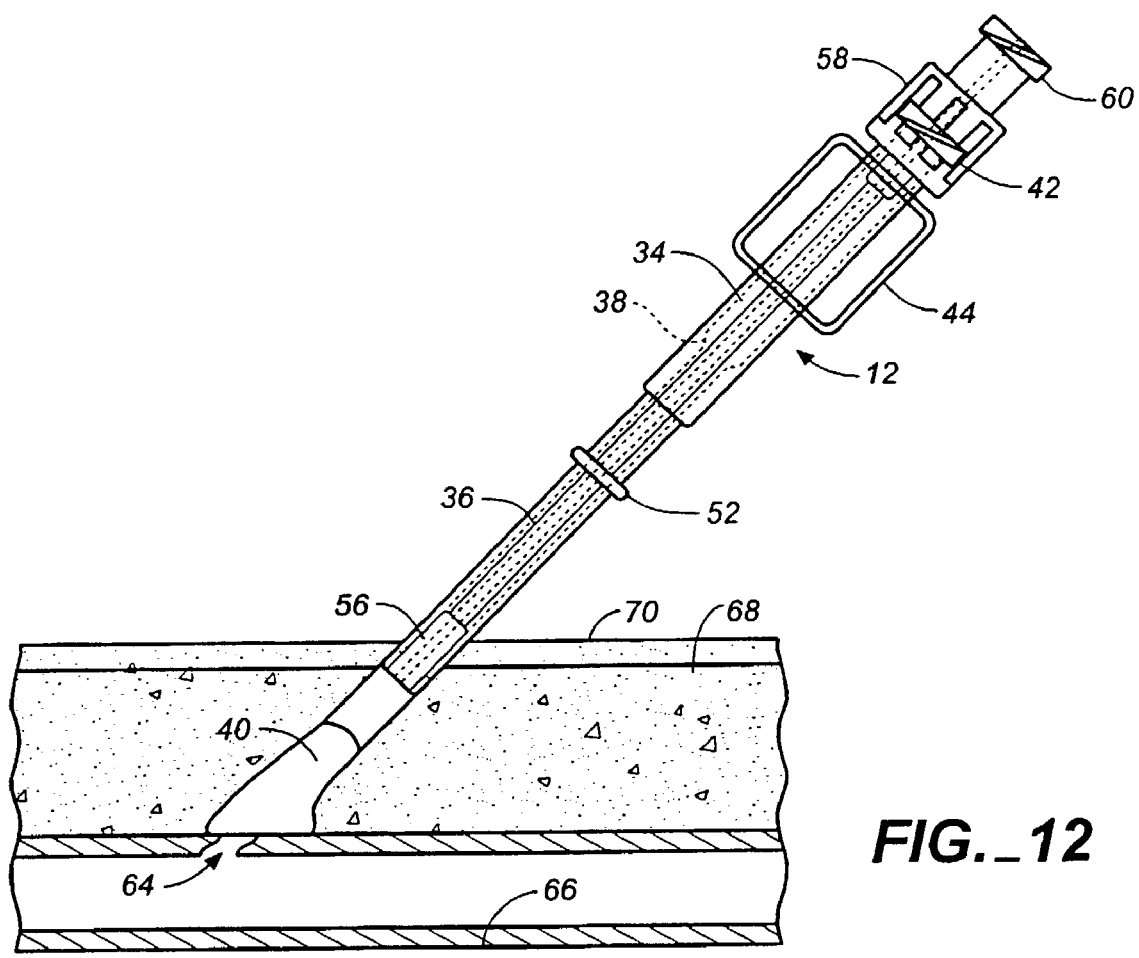
FIG._12
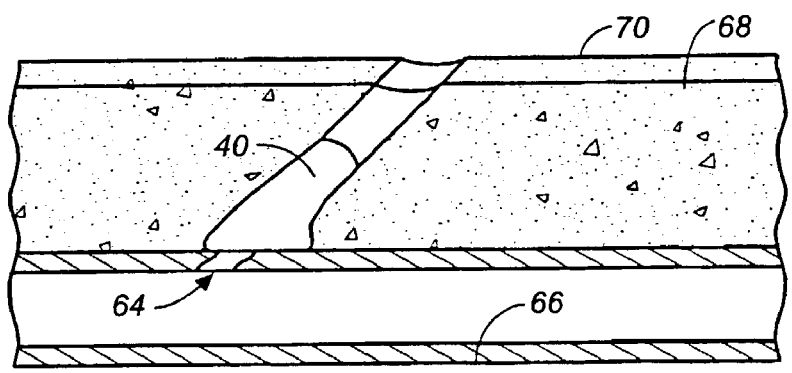
FIG._13

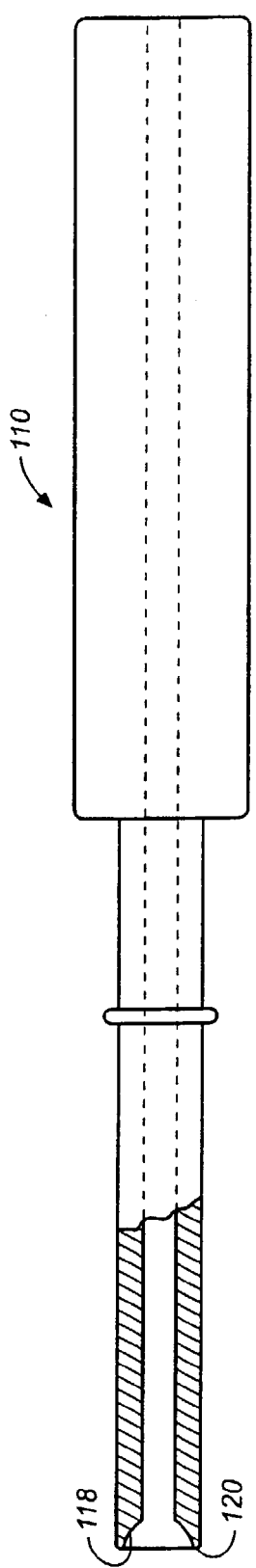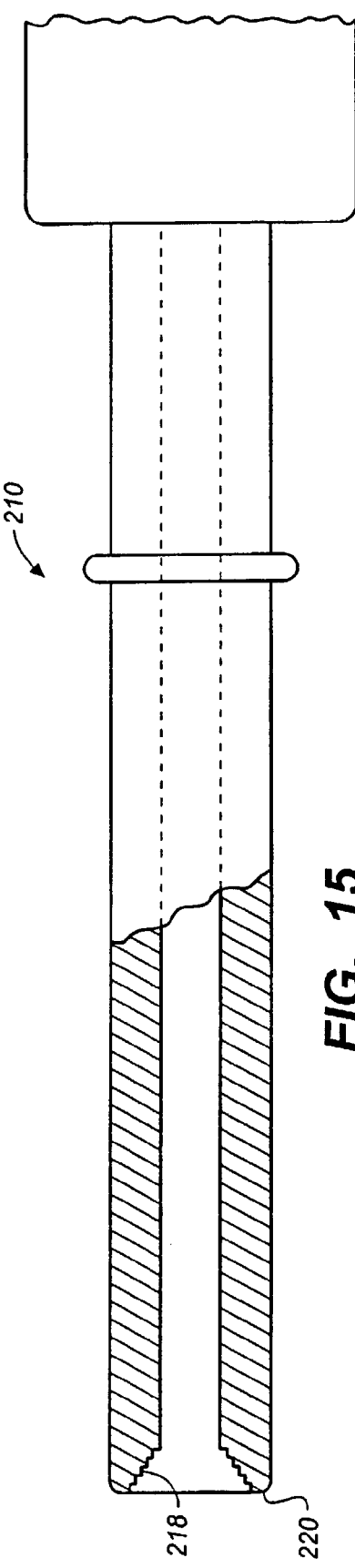

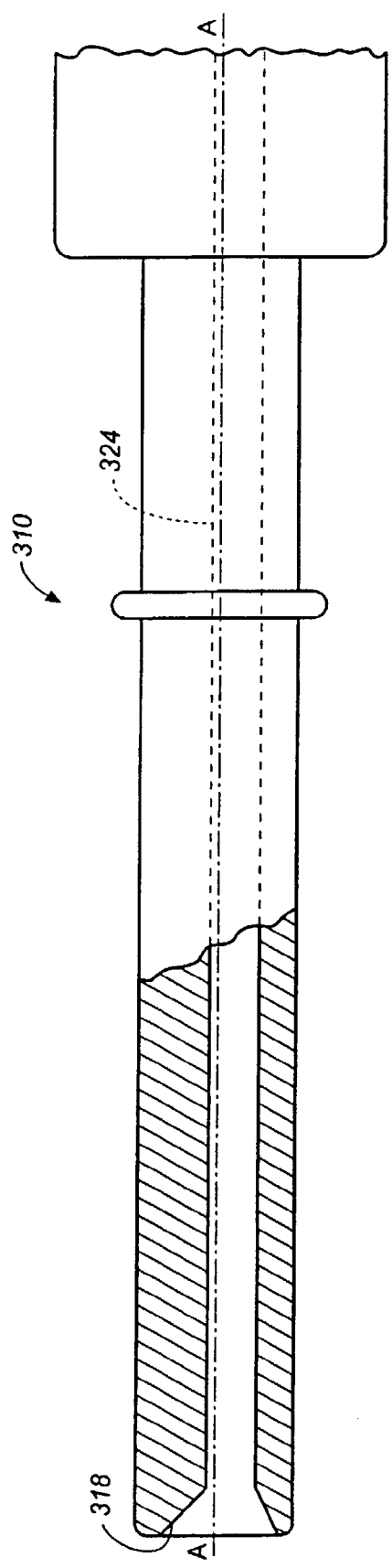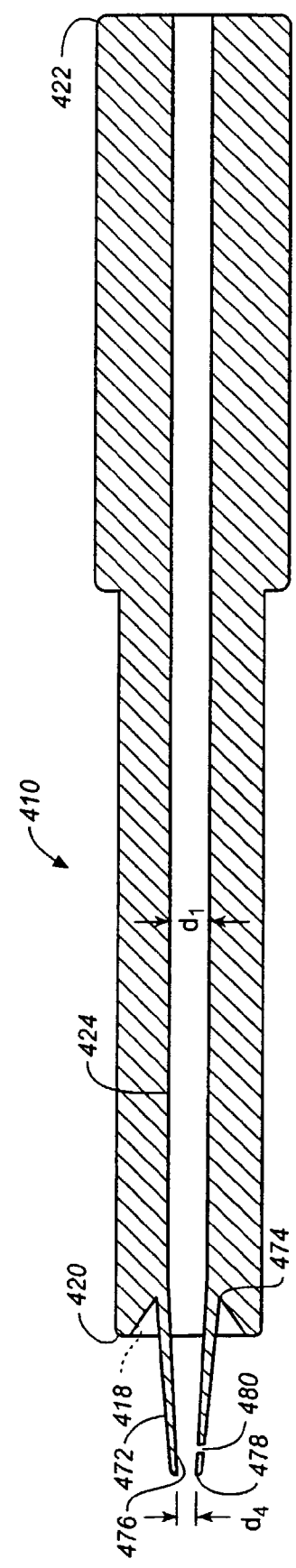

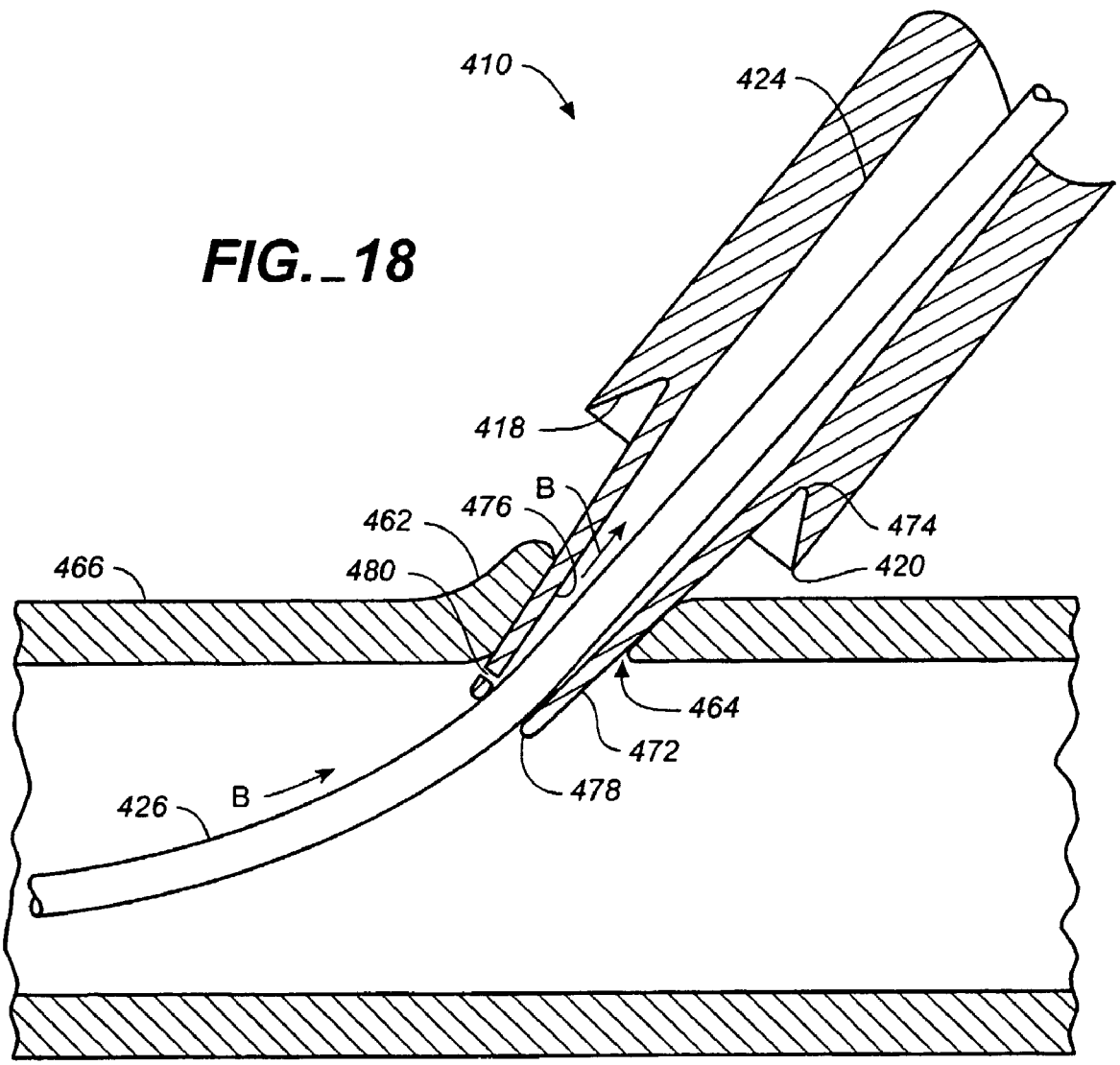
FIG._18

FIG._19
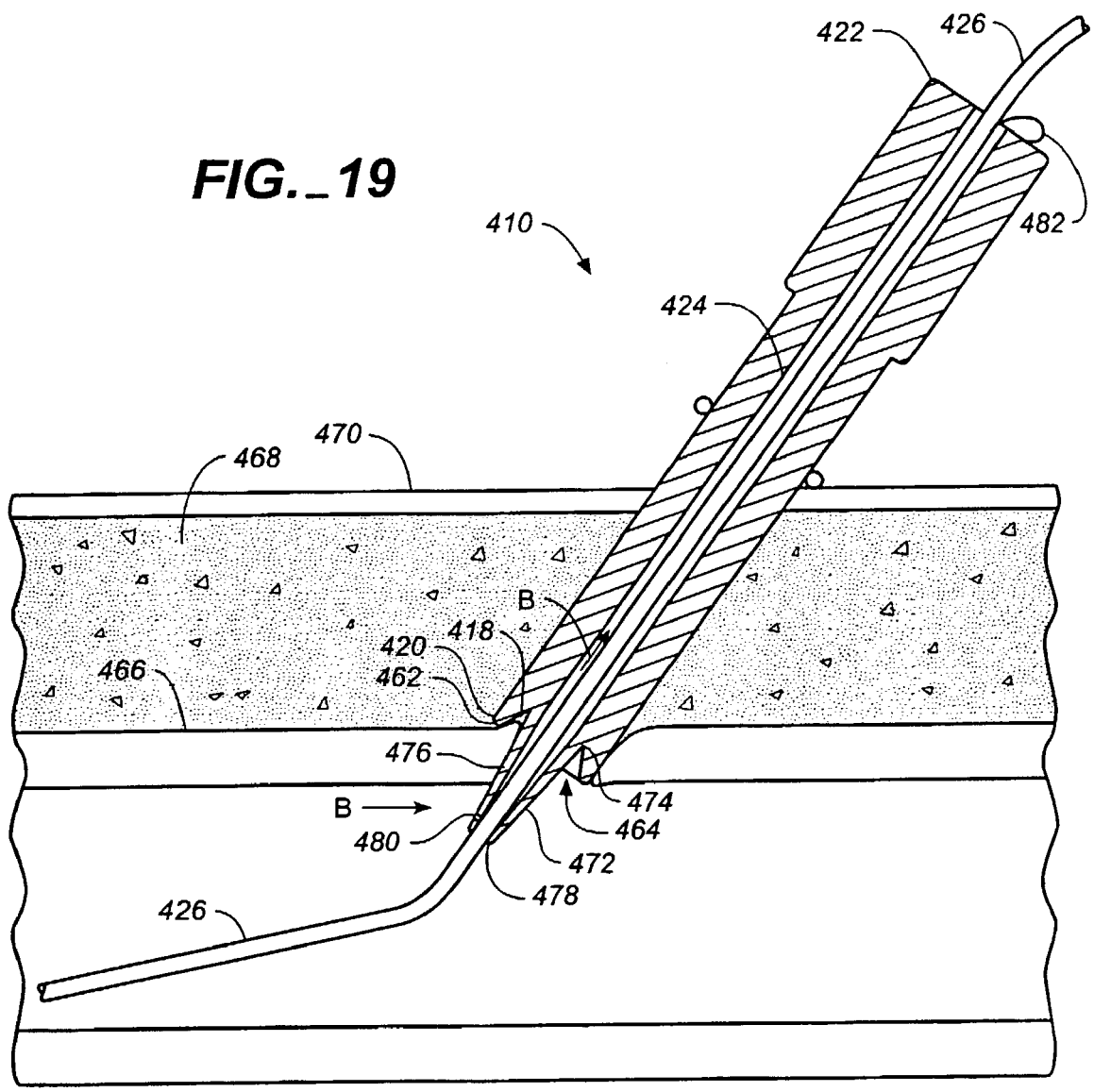

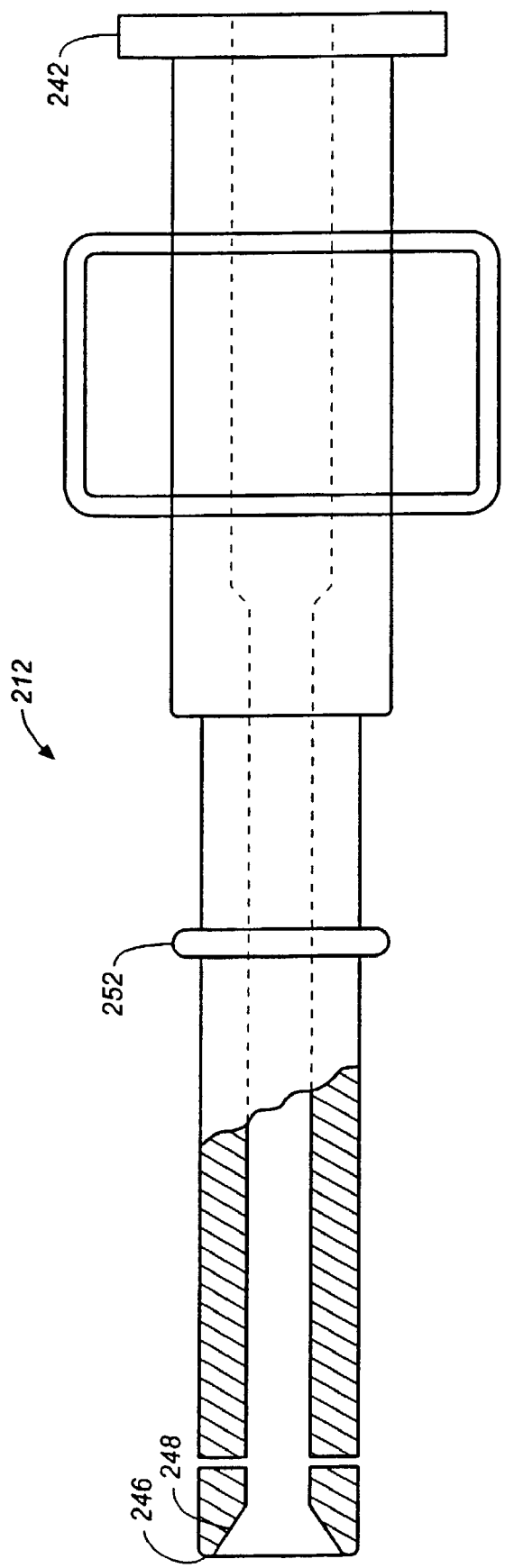

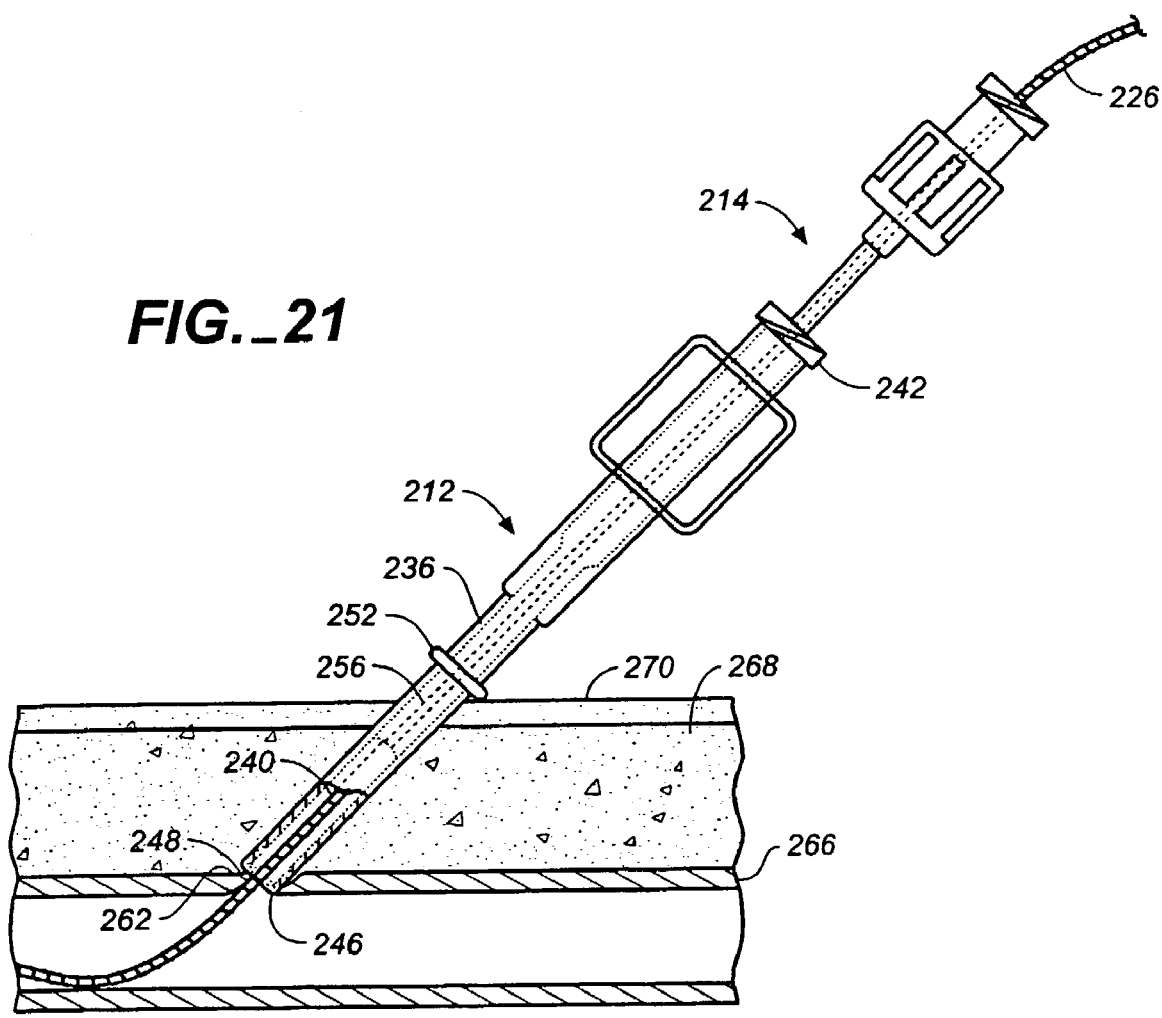
FIG._21

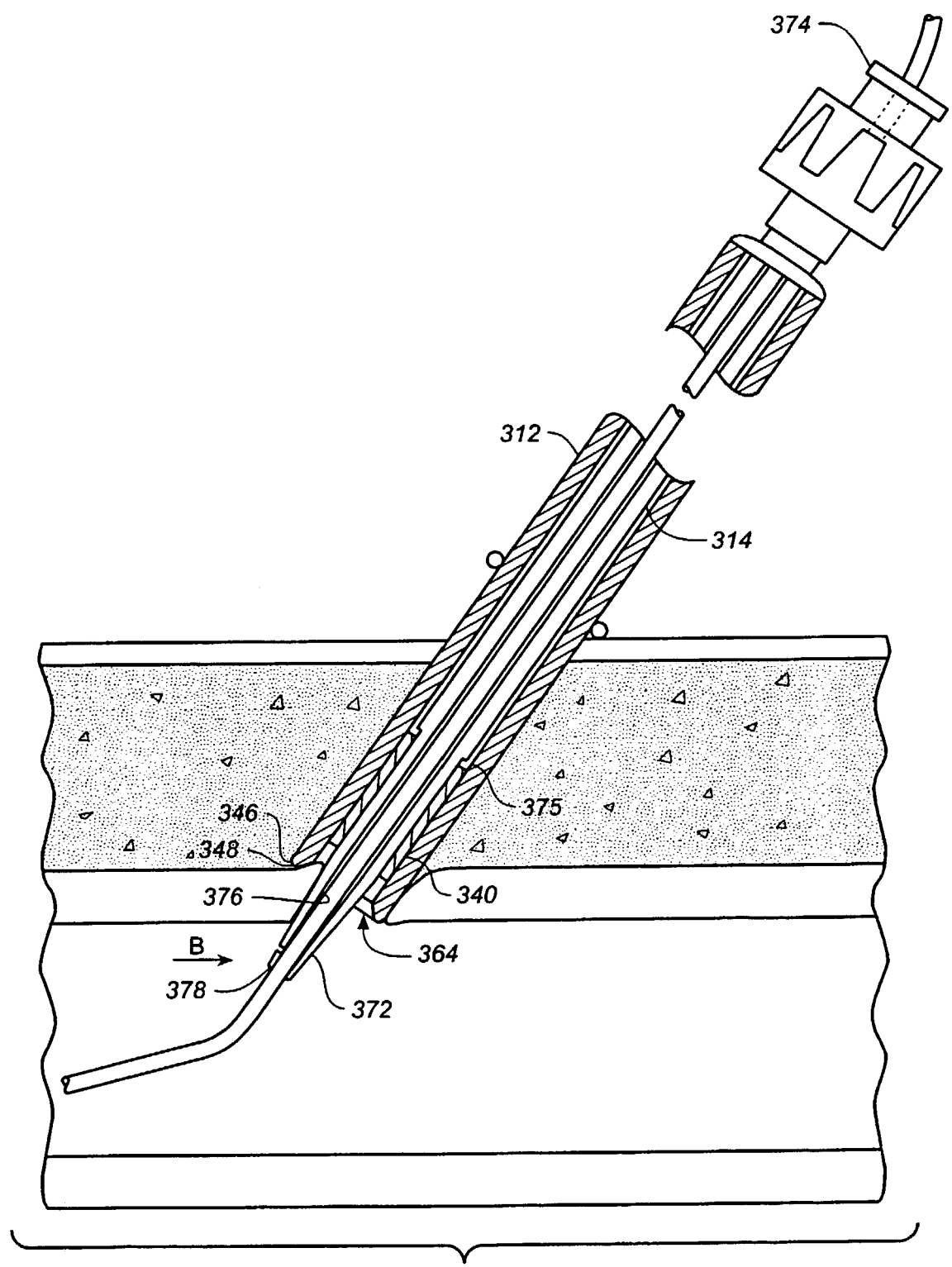
FIG._22

DEVICE AND METHOD FOR DETERMINING A DEPTH OF AN INCISION

BACKGROUND OF THE INVENTION

1. Field of the Invention

The invention relates to a device and method for determining a depth of an incision for deployment of a closure system for blood vessel punctures.

2. Brief Description of the Related Art

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal anchor may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such as cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Such puncture sealing devices are generally used in conjunction with a cannula or arterial dilator which dilates an access tract in the tissue before inserting the sealing device for placing the intraluminal or sealing plug. By using the cannula to dilate the access tract, the sealing device can be easily advanced into the tissue toward the vascular puncture. A conventional cannula C having a constant diameter lumen which is sized to closely accommodate a guidewire is shown in FIG. 1. Alternatively, the cannula may have a lumen with a diameter which narrows at the distal end. When these conventional cannulas are advanced into the access tract, the cannulas often encounter scar or muscular tissue that requires substantial force to advance the cannula through these layers. As shown in FIG. 1, the cannula C which has a constant diameter lumen may enter the vascular puncture while being advanced into the access tract, or the cannula C will bounce against a wall of the blood vessel rather than accurately locate the blood vessel wall. A dilator D, shown in FIG. 2, has a tapered distal end for dilating a tissue access tract. The tapered dilator D cannot accurately locate a puncture because the distal end of the dilator passes through the blood vessel puncture. Accordingly, the sealing plug may not be accurately placed over the puncture site when a sealing device is used with the cannula C or the dilator D.

Accordingly, it would be desirable to provide a device and method for accurately determining the depth of an incision by accurately locating the blood vessel wall for properly placing a hemostasis promoting plug over the puncture site.

SUMMARY OF THE INVENTION

The present invention relates to a device and method for accurately determining the depth of an incision that extends from the epidermal layer to the blood vessel wall for properly placing a hemostasis promoting plug over a puncture site.

In accordance with one aspect of the present invention, a device for determining a depth of an incision that extends from the epidermal layer to a blood vessel includes an elongated member including a distal end and a proximal end, the distal end having means for locating the blood vessel while impeding the distal end of the elongated member from entering the blood vessel.

In accordance with another aspect of the present invention, a device for determining a depth of an incision that extends from an epidermal layer to a blood vessel puncture site includes an elongated member having a distal end, a proximal end, and means at the distal end for locating the blood vessel puncture site by capturing an edge of the blood vessel puncture and a control member extending from the distal end of the elongated member and configured to be received in the puncture site.

In accordance with an additional aspect of the present invention, a method for determining a depth of an incision that extends from the epidermal layer to a puncture in a blood vessel includes the steps of introducing an elongated member through the incision, the elongated member having a proximal end, and a distal end configured for locating a blood vessel while preventing the distal end of the elongated member from entering the blood vessel, locating the blood vessel by receiving a portion of a wall of the blood vessel with the distal end, and setting a depth indicating member to mark a depth of the puncture in the blood vessel.

In accordance with a further aspect of the invention, a method for determining a depth of an incision that extends from an epidermal layer to a puncture in a blood vessel includes the steps of introducing an elongated member through the incision and providing visual feedback of a general location of the blood vessel puncture by venting blood through the elongated member and providing specific tactile feedback of a specific location of the blood vessel puncture by contact between the elongated member and an exterior of the blood vessel puncture.

The present invention provides a device and method which accurately determines the location of the blood vessel for properly placing a hemostasis over a puncture site.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a side cross sectional view of a punctured blood vessel and constant diameter arterial dilator in accordance with the prior art;

FIG. 2 is a side cross sectional view of a punctured blood vessel and tapered arterial dilator in accordance with the prior art;

FIG. 3 is a top view of a blood vessel puncture sealing kit;

FIG. 4 is a partial cross sectional side view of a tract dilator having a tapering section at the distal end;

FIG. 5 is an enlarged side cross sectional view of a portion of FIG. 4;

FIG. 6 is a side cross sectional view of a punctured blood vessel and a tract dilator for locating the puncture;

FIG. 7 is an enlarged partial side cross sectional view of the punctured blood vessel and the tract dilator of FIG. 6;

FIG. 8 is a side view of an introducer having a pledget positioned within the introducer staging chamber and a syringe attached to the introducer;

FIG. 9 is a side view of the introducer and syringe of FIG. 8 with the pledget hydrated and advanced to a delivery chamber within the introducer;

FIG. 10 is a side cross sectional view of a punctured blood vessel with the introducer and plunger positioned for delivery of the pledget;

FIG. 11 is a side cross sectional view of a punctured blood vessel with the pledget being deposited at the puncture site;

FIG. 12 is a side cross sectional view of a punctured blood vessel with a hydrated pledget deposited at the puncture site, the guidewire removed, and the delivery system being withdrawn;

FIG. 13 is a side cross sectional view of a punctured blood vessel with a hydrated pledget facilitating hemostasis of the puncture site;

FIG. 14 is a partial cross sectional side view of a tract dilator which has a distal end with an internal concave shape;

FIG. 15 is a partial cross sectional side view of a tract dilator which has a distal end with an internal stepped shape;

FIG. 16 is a partial cross sectional side view of another embodiment of a tract dilator which has an off-center lumen and an off-center distal end opening;

FIG. 17 is a side view of an additional embodiment of a tract dilator with a control member extending from the distal end;

FIG. 18 is an enlarged side cross sectional view of a punctured blood vessel and the tract dilator of FIG. 17;

FIG. 19 is a side cross sectional view of the embodiment of FIG. 17 with the tract dilator abutting the blood vessel;

FIG. 20 is a partial cross sectional side view of an additional embodiment of an introducer having an interior tapering section at a distal end for depth determination;

FIG. 21 is a side cross-sectional view of a punctured blood vessel and the introducer of FIG. 20; and FIG. 22 is a partial side cross-sectional view of a punctured blood vessel and an alternative embodiment of an introducer and a pusher with a control member extending from the distal end.

DETAILED DESCRIPTION OF THE PREFERRED EMBODIMENTS

The device and method for determining a depth of an incision according to the present invention is used in connection with a delivery system for delivery of a bio-compatible sponge in a hydrated condition to a blood vessel puncture site to achieve hemostasis. In kit form, as shown in FIG. 3, an over-the-wire delivery system for delivery of a bio-compatible sponge includes a tract dilator 10, an introducer 12, and a pusher 14. This system allows over the wire delivery of the sponge material directly to the puncture site to achieve hemostasis. Over-the-wire delivery ensures that the sponge material is properly positioned to fully occlude the puncture. In addition, the sponge material is delivered in a hydrated state which immediately expands to stop blood flow through the puncture. The introducer allows the delivery of more sponge material through a smaller tract by hydrating and compressing the absorbable sponge material.

Prior to discussing the present invention in further detail, the following terms are defined:

"Pledget" means a piece of sponge formed into a generally elongated shape having a size which allows delivery in a hydrated state through a delivery cannula or introducer to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which when implanted within a human or other mammalian body is absorbed by the body.

"Hydrate" means to partially or fully saturate with a fluid, such as, saline, water, contrast agent, thrombin, therapeutic agents, or the like.

"Kneading" of the absorbable sponge material means both dry and wet manipulation of sponge material which compresses, enlarges, or changes the shape of the sponge material causing the sponge material to have improved expansion response.

The tract dilator 10, as illustrated in FIGS. 3–7, includes a stem-portion 32, a proximal end 22, a distal end 20, and a lumen 24 extending from the proximal end to the distal end of the tract dilator. The lumen 24 is provided to allow the tract dilator 10 to be received over a guidewire 26, which extends through the puncture wound 64 into the blood vessel 66. The diameter $d_1$ of the lumen 24 is about 0.040 to 0.120 inches, preferably about 0.050 to 0.090 inches, and should loosely accommodate a guidewire 26, as shown in FIGS. 6 and 7.

The stem-portion 32 of the tract dilator 10 may have a constant outer diameter $d_3$ or may taper slightly to a smaller outer diameter at the distal end 20. The outer diameter $d_3$ of the tract dilator distal end 20 is configured so that the tip of the tract dilator will not pass into the blood vessel 66 but will stop and provide tactile feedback when it reaches the external wall of the blood vessel. The distal end 20 can be provided with rounded edges 28 to prevent catching on subcutaneous tissue 68 as the tract dilator 10 is inserted through the epidermal outer layer 70 and subcutaneous tissue 68 to the blood vessel puncture site 64.

An internal tapering surface 18 is provided at the distal end 20 of the tract dilator 10. The tapered surface 18 extends from the lumen 24 having a diameter $d_1$ to the distal end 20 which has an internal larger diameter $d_2$. As shown most clearly in FIG. 5, the tapering surface 18 forms an angle θ, relative to a longitudinal axis A of the tract dilator 10. The angle θ can range from 0° to 90°. Preferably, the angle θ formed between the tapering surface 18 and the longitudinal axis A of the tract dilator 10 is about 20° to 70°. The diameter $d_2$ of the distal opening should be greater than 50% of the outer diameter $d_3$ of the tract dilator, but can range from 20% to 100%, preferably about 50% to 90% of the outer diameter $d_3$. The length L of the tapering surface 18 is about 0.010 inches or larger, preferably about 0.020 to 0.100 inches. The tapering surface 18 provides a means for locating the blood vessel while impeding the distal end of the dilator 10 from entering the blood vessel.

A depth indicator 30 is positioned around the stem portion 32 of the tract dilator 10 and is movable in an axial direction. Once the tract dilator 10 has been inserted until the distal end 20 abuts the external wall of the blood vessel 66, as shown in FIGS. 6 and 7, the depth indicator 30 is manually positioned near the epidermal outer layer 70 of the patient's skin. Alternatively, the depth indicator 30 can be pushed to a depth indicating position adjacent to the epidermal outer layer 70 as the dilator is inserted. Preferably, the depth indicator 30 is an elastic ring which is slidably movable in an axial direction on the tract dilator 10 and maintains a measured position for comparison with the introducer 12.

The elongated member 32 is made of a material with a hardness not lower than 50 D durometer. In addition, a portion of the elongated member 32 is provided with a friction reducing material resulting in the outer surface of the elongated member having a low friction resistance.

FIGS. 8–13 illustrate steps for delivery of a sponge pledget accurately to a blood vessel puncture site after the depth of the incision has been determined. The introducer 12, shown in FIGS. 8 and 9, includes a staging chamber 34 for receiving a sponge pledget 40 and a delivery chamber 36 for receipt of a hydrated and compressed pledget from the staging chamber. A tapered section 38 is provided between the staging chamber 34, which has a larger diameter lumen, and the delivery chamber 36, which has a smaller diameter lumen. The tapered section 38 of the introducer 12 acts as a compression member to compress the hydrated pledget 40 into the delivery chamber. The introducer 12 also includes a luer fitting 42 at a proximal end for connection to a conventional syringe and wing members 44 for use in grasping the introducer.

The sponge pledget 40 is formed from a sheet of sponge material which has been cut into a rectangular shape and rolled to form a compact, substantially cylindrical, elongated pledget. The pledget 40 is sized to be received within the staging chamber 34 of the introducer 12 in a dry rolled state.

Once the pledget 40 has been inserted into the staging chamber 34 of the introducer 12, a conventional syringe 50 containing a hydrating fluid, such as saline, is connected to the luer fitting 42, as shown in FIG. 8. The pledget 40 is then hydrated within the staging chamber 34 by injecting a fluid into the staging chamber from the syringe 50 causing the pledget to swell, partially or fully blocking the lumen of the introducer. The partial hydration or wetting of the exterior surface of the pledget 40 creates a lubricous surface on the pledget. The hydrated pledget 40 is then forced into the delivery chamber 36 by injecting additional fluid with the syringe 50 to force the pledget through the tapered section 38 to the delivery chamber 36. For a somewhat smaller pledget 40 which does not entirely block the lumen of the introducer 12 after hydrating, the venturi effect will help draw the pledget into the delivery chamber 36.

As shown in FIG. 9, a finger may be placed over the distal end of the introducer 12 during delivery of the pledget 40 to the delivery chamber 36 to prevent the pledget from being ejected from the introducer by the pressure of the fluid. Preferably, one or more vent holes 46 are provided in the side walls of the introducer adjacent the distal end to allow air and liquid to escape from the introducer while the pledget 40 is positioned for delivery. These vent holes 46 are small enough to prevent the pledget 40 from passing substantially into or through the vent holes.

The introducer 12 also includes a depth indicator 52 which is an axially movable member used to indicate the depth to which the introducer should be inserted into the patient to achieve the proper positioning of the pledget 40 at the puncture site 64. The depth indicator 52 of the introducer 12 is aligned with the depth indicator 30 on the tract dilator 10 to achieve proper pledget positioning.

The introducer 12 may be formed in any known manner such as by injection molding from a plastic material. Preferably, the introducer 12 is transparent so that the pledget 40 can be viewed through the introducer and the user can visually confirm the pledget position. The introducer lumen may be provided with a friction reducing coating for improved pledget delivery. The delivery fluid also reduces friction for improved delivery by wetting the exterior surface of the pledget.

The pusher 14, as illustrated in FIGS. 3 and 10, includes a distal end 56 which is configured to slide within the lumen of the delivery chamber 36 of the introducer 12. Preferably, there is a very small clearance or a resilient interference between the outer diameter at the distal end 56 of the pusher 14 and the inner diameter of the delivery chamber 36 to prevent portions of the pledget from getting caught between the pusher and the introducer 12. A resilient pusher distal end 56 or a sealing member on the pusher 14 may be used to accomplish or approach a resilient fit between the introducer 12 and the pusher.

The pusher 14 also may include a male luer fitting 58 for connecting the proximal end of the pusher to the proximal end of the introducer 12 after pledget delivery. The male luer fitting 58 acts as a stop to limit the motion of the pusher 14 with respect to the introducer 12. When the pusher 14 is locked to the introducer 12, the two may be used together to apply localized compression to the puncture site 100. A female luer fitting 60 may also be included at the proximal end of the pusher 14 for connection of a syringe to the pusher for injection of a beneficial agent through the pusher.

One method of delivering an absorbable sponge pledget 40 to facilitate hemostasis of a blood vessel puncture wound 64 will now be described with respect to the steps illustrated in FIGS. 6–13. After an intravascular procedure has been completed, a guidewire 26 is already in an incision and passes through the subcutaneous tissue 68 into the blood vessel 66. Alternatively, if a guidewire 26 is not already in place, then the guidewire is inserted through an access sheath used in the intravascular procedure and the access sheath is then removed. The guidewire 26 is maintained in the incision with a proximal end extending from the patient's body and a distal end extending through the epidermal outer layer 70 and subcutaneous tissue 68, through the blood vessel puncture 64, and into the blood vessel 66. The guidewire 26 has a certain stiffness so that it raises the anterior proximal lip 62 of the blood vessel 66. Preferably, in a region proximal to the anterior proximal lip 62, the guidewire 26 has a stiffness which is equal to or greater than that of a 0.025" diameter, 300 series stainless steel wire. By advancing the tract dilator 10 over a guidewire which has a certain stiffness, the guidewire guides the tract dilator and prevents said tract dilator from catching on the subcutaneous tissue as the dilator advances in the incision. Additionally, a guidewire which has a small diameter can favorably raise the anterior proximal lip 62 of the blood vessel 66.

As discussed above, the tract dilator 10 is threaded over the guidewire 26 and advanced down into the incision through the subcutaneous tissue 68 to an exterior wall of the blood vessel 66. Resistance is felt when the tract dilator distal end 20 contacts the exterior wall of the blood vessel 66 since the tract dilator 10 is configured to resist passing through the blood vessel puncture 64 and into the blood vessel. The tract dilator distal end 20 receives the raised anterior proximal lip 62 of the blood vessel 66 (shown in FIG. 7) and impedes the distal end from entering the blood vessel. By attempting to further insert the tract dilator 10 into the incision, the guidewire 26 biases the anterior proximal lip 62 toward the tapering surface 18, thereby catching said anterior proximal lip and providing further resistance. Thus, the tract dilator 10 provides tactile feedback to the user of the blood vessel location. The dilator is advantageously made from a stiff or rigid material, providing an enhanced ability to advance through subcutaneous tissue and providing one-to-one tactile feedback to the user. Such stiff material may comprise any suitable material including, but not limited to, rigid polyvinyl chloride (PVC), polycarbonate, or a metal such as stainless steel.

The outside surface of the stem-portion 32 of the tract dilator 10 is preferably provided with a friction reducing overlay to facilitate advancing the tract dilator through the subcutaneous tissue 68. By reducing the amount of force necessary to advance the tract dilator 10 through tissue layers, the user can more easily distinguish when the tract dilator is passing through subcutaneous tissue as compared to contacting the exterior of the blood vessel. The friction reducing overlay is selected such that the coefficient of friction between the outside surface of the stem portion 32 and subcutaneous tissue 68 is reduced by about 10%, preferably by about 20%, more preferably by 30%, yet more preferably by about 40%, and more preferably by about 50%, and yet more preferably by more than 50%. The friction reducing overlay may also be provided on the walls of the lumen 24 to facilitate introducing the tract dilator 10 over the guidewire 26.

The depth indicator 30 on the tract dilator 10 is moved to abut the epidermal layer 70, thereby indicating a distance from the outer skin surface to the blood vessel puncture site 64. The tract dilator 10 is then removed over the guidewire 26 and the introducer depth indicator 52 is aligned with the tract dilator depth indicator 30.

A sheet of sponge material is cut into a rectangle, is rolled tightly to form a pledget 40, and is placed into the staging chamber 34 of the introducer 12. The steps of cutting and rolling the pledget 40 and placing the dry pledget in the introducer staging chamber 34 may be performed before or after the intravascular procedure. Alternatively, the introducer 12 may be provided preloaded with a prepared pledget 40. With the pledget 40 placed in the introducer, the syringe 50 is filled with a hydrating fluid such as saline, thrombin, contrast agent, other therapeutic agent, or the like and attached to the introducer 12, as illustrated in FIG. 8. Fluid is injected slowly into the introducer 12 to hydrate the pledget 40. The user then pauses to allow hydration and initial swelling of the pledget 40. Sufficient hydration may occur in about 20 to 30 seconds or less depending on the size of the pledget 40.

As shown in FIG. 9, the user then places a finger over the distal end of the introducer 12 and injects fluid with the syringe 50 to force the pledget 40 through the tapered section 38 and into the smaller end or delivery chamber 36 of the introducer 12. Injection of fluid is stopped when the pledget 40 is positioned at the distal end of the delivery chamber 36. At this point the syringe 50 is removed and the introducer is loaded over the proximal end of the guidewire 26 for the delivery of the pledget 40 to the puncture site.

As shown in FIG. 10, a proximal end of the guidewire 26 is fed into the distal end of the introducer 12 though the hydrated and compressed pledget 40 and out the proximal end of the introducer. Preferably, the guidewire 26 is fed through substantially the center of the pledget 40 to ensure that the implanted pledget is centered over the blood vessel puncture 64. Alternatively, the guidewire may be inserted along a side of the pledget 40, through a separate second lumen of the introducer, through an axial lumen in the pledget, or through a low density center of the pledget.

After feeding the guidewire 26 through the introducer 12, the guidewire 26 is fed through the pusher 14 and the pusher is advanced into the introducer until the distal end 56 of the pusher is in contact with the pledget 40. The introducer 12 and pusher 14 are then advanced together down though the epidermal layer 70 and the subcutaneous tissue 68 until the depth indicator 52 on the exterior of the introducer is at the skin level.

In the step illustrated in FIG. 11, the pusher 14 is held stationary while the introducer 12 is withdrawn proximally preferably to a distance of about 75% of the length of the compressed, hydrated pledget 40. This 75% withdrawal distance may be indicated with an appropriate marker on the introducer 12 or the plunger 14 or by contact between the fittings 42, 58 of the introducer and plunger. The portion of the pledget 40 ejected into the tissue quickly expands upon delivery to fill the available space and provide localized compression. With the pusher 14 and introducer 12 in the position illustrated in FIG. 11 and the pledget 40 partially ejected, a slight forward pressure is maintained by the operator on the introducer and pusher to increase local compression for a period of time of approximately 1 minute to allow hemostasis to begin. The forward pressure causes the pledget 40 to be compressed around the puncture site, as shown in FIG. 11.

The guidewire 26 is then completely removed from the introducer 12 and the pusher 14. The introducer 12 is withdrawn the remaining approximately 25% by engaging the fitting 58 of the pusher with the female luer fitting 42 of the introducer to completely discharge the pledget 40 into the subcutaneous tissue 68 above the puncture site 64. A slight forward pressure can then be maintained by the operator on the introducer 12 and pusher 14 for approximately 1 minute before the introducer and pusher are removed from the tissue tract, as shown in FIG. 12, leaving the sponge pledget 40 positioned against the outer vessel wall, as shown in FIG. 13, providing local compression and facilitating hemostasis. The delivered pledget 40 maintains hemostasis until healing of the blood vessel 66 occurs. The pledget 40 is absorbed by the body over time.

One type of absorbable sponge material which is acceptable for use in the present invention is Gelfoam™, manufactured by the Pharmacia & Upjohn Company. Gelfoam™ is a porous, pliable, cross-linked gelatin material and is available commercially in sheet form as pre-compressed or non-compressed sponge. The material may be provided preformed as a pledget 40 or may be cut with a punch, or a stencil, or template and knife and rolled to form a pledget as described above. Once hydrated, the pledget 40 can be easily compressed to fit into a lumen having a smaller cross sectional area than the original cross sectional area of the pledget. Additionally, the kneading of the hydrated pledget 40 during delivery encourages air trapped within the Gelfoam™ to be expelled and replaced with fluid, allowing rapid expansion upon delivery. When a pledget 40 of a pre-compressed Gelfoam™ is hydrated and kneaded (expelling air) during delivery, the pledget will have the absorption capacity to rapidly expand to many times (e.g., 3 or more times) its original dry volume upon delivery. When a pledget 40 of the non-compressed Gelfoam™ is hydrated and kneaded (expelling air) during delivery, the pledget will have the absorption capacity to rapidly expand to its original dry volume upon delivery. These properties make the Gelfoam™ sponge material particularly useful for facilitating hemostasis of blood vessel punctures.

Abrupt lumen diameter changes within the introducer 12, such as at the tapered section 38, will improve "kneading" of the absorbable sponge material passing through the introducer. Manipulation of the dry absorbable sponge material, such as the rolling of the pledget 40, also provides kneading. Kneading improves hydration of the sponge material thereby improving the expansion properties of the hydrated delivered absorbable sponge.

As illustrated in FIG. 14, an alternative embodiment of a tract dilator 110 is substantially similar to the embodiment shown in FIG. 4, except that the tapering surface 118 has a substantially concave spherical shape. It is understood that the tapering surface 118 may further be formed as a convex surface, counterbore, or any form known to those skilled in the art.

A further embodiment of a tract dilator 210 is substantially similar to the embodiment of FIG. 4, except that the tapering surface 218 is a generally stepped configuration, as shown in FIG. 15. Where the tapering surface 218 has a generally stepped configuration, the distal end 220 of the tract dilator 210 can further provide a means to capture the external blood vessel wall and thereby provide the user with additional tactile feedback.

In the embodiment of FIG. 16, a tract dilator 310 has a substantially similar structure as in FIG. 4, except that the lumen 324 is off-center from the longitudinal axis A of the tract dilator. Preferably, the lumen is off-set by a distance such that a portion of the tapering surface 318 which is positioned to receive the anterior proximal lip has the maximum radial extension from said lumen.

Another alternative embodiment of a tract dilator 410 is illustrated in FIG. 17 in which an extending control member 472 extends from the tapering surface 418 and beyond the distal end 420 of the tract dilator 410. The extending control member 472 is configured to provide feedback means from the blood vessel to the user. Such feedback indicates to the user that the tract dilator is advancing in the desired direction toward the blood vessel. The extending control member 472 includes a proximal end 474, a distal end 478, and a lumen 476 which extends from the proximal end to the distal end. The lumen 476 is sized to accommodate a guidewire 426. The distal end 478 has at least one vent hole 480. The lumen 476 tapers from a first diameter at the proximal end 474 to a second, smaller diameter at the distal end 478 in which the distal end fits closely around the guidewire. The lumen 476 of the extending control member 472 is in fluid communication with the lumen 424 of the tract dilator 410. The extending control member 472 extends from the tapering surface 418 of the tract dilator 410 by about 0.10 to 6 inches, preferably by about 3 to 5 inches.

As shown in FIG. 18, after the lumen 424 of the tract dilator 410 is introduced over a guidewire 426, the tract dilator is advanced into the incision through the subcutaneous tissue 468 to an outside surface of the blood vessel 466. Before the distal end 420 of the dilator 410 abuts the external wall of the blood vessel 466 at the puncture wound 464, a portion of the extending control member 472 passes into the blood vessel. A close fit between the distal end 478 and the guidewire 426 prevents fluid in the blood vessel 466 from entering into the lumen 476 at that location; however, as the extending control member 472 advances further into the blood vessel, blood may enter into the lumen of the extending member through the vent hole 480, in the direction of arrow B. The extending member 472 is preferably manufactured from a flexible material to prevent said extending member from catching on subcutaneous tissue 468 as said member advances through the patient's skin and tissue to the puncture site 464.

The blood 482 exits the lumen 424 in the tract dilator 410 at the proximal end 422, as illustrated in FIG. 19, therein providing the user with visual feedback that the dilator is approaching the desired location with respect to the blood vessel 466. Then when the distal end 420 of the dilator 410 abuts the wall of the blood vessel 466 at the puncture site 464, resistance is felt since the tract dilator 410 is configured to resist passing through the blood vessel puncture and into the blood vessel. The tapering surface 418 at the distal end 420 receives the anterior proximal lip 462 of the blood vessel 466 and impedes the distal end from entering said blood vessel. By attempting to further insert the tract dilator 410 into the incision, the guidewire 426 biases the anterior proximal lip 462 toward the tapering surface 418, thereby catching said anterior proximal lip and providing the user tactile feedback that the blood vessel 466 has been located. Accordingly, this provides the user with visual and tactile feedback when the tract dilator is used to locate the blood vessel wall.

The exterior surface of extending control member 472 further provides the benefit of limiting or preventing fluid from exiting out of the puncture site 464 since the extending member will substantially occlude said puncture 464. Thus, the extending member 472 prevents fluid from exiting the blood vessel through the puncture site and into the surrounding tissue and controls the puncture site. Alternatively, by partially occluding the puncture site 464, the extending control member 472 allows the physician to prevent fluid from exiting the blood vessel through said puncture and into the surrounding tissue by applying pressure. Typically, pressure is applied at the epidermal surface at a position directly over or proximal to the puncture site 464. It is understood that the extended member can be provided without a vent 480 if controlling the amount of fluid from exiting the blood vessel through the puncture site is the only additional benefit desired.

Although the use of a tract dilator 10 has been described above, the introducer 12 can be used in place of the tract dilator, and the depth determining step can be performed while inserting the introducer, particularly where a plastic sheathed guidewire, other friction reducing guidewire, or other friction reducing feature is used. The use of the introducer 12 as the dilator eliminates errors which may occur in accurately setting the depth indicator 52 on the introducer.

As shown in FIG. 20, an alternative embodiment of an introducer 212 includes a distal end 246, a proximal end 242, and a tapering interior surface 248 at the distal end. The tapering surface 248 has a substantially similar structure and function to the tapering surface 18 of the tract dilator 10. As illustrated in FIG. 21, a guidewire 226 is fed into the distal end 246 of the introducer 212 through the hydrated and compressed pledget 240 and out the proximal end 242 of the introducer. The guidewire 226 has a certain stiffness so that it raises the anterior proximal lip 262 of the blood vessel 266. The guidewire 226 is fed through the pusher 214, and the pusher is advanced into the introducer until the distal end 256 of the pusher is in contact with the pledget 240. The introducer 212 and pusher 214 are advanced together down into the incision through the subcutaneous tissue 268 to an outside surface of the blood vessel 266. The introducer distal end 246 receives the raised anterior proximal lip 262 of the blood vessel and impedes the distal end from entering said blood vessel. Once the introducer 212 has been inserted until the distal end 246 abuts the external wall of the blood vessel 266, the pledget can be delivered in the manner described previously.

As shown in FIG. 22, a pusher 314 is positioned internally of an introducer 312 as described above with a tapering internal surface 348. The pusher 314 has a proximal end 374 and a distal end 378 including a step 375 and an extending control member 372. The extending control member 372 includes a lumen 376, the lumen extending from the proximal end to the distal end. The extending control member 372 is configured to provide feedback means from the blood vessel 366 to the user and control of the puncture site in a substantially similar manner as with the tract dilator extending control member 472 of FIGS. 17 and 18. The feedback from the blood vessel 366 indicates to the user that the introducer 312 is advancing in the desired direction toward the blood vessel. The pledget 340 can be delivered as described above, with the additional benefit of the extending control member 472.

A further embodiment of an introducer/pusher system may be used for dilation in which the pusher or obturator used during dilation and depth determination is different from the pusher which is used for delivery of the pledget. The pusher for use during dilation preferably has a luer lock at a proximal end which locks to the proximal end of the introducer and has a length such that the distal ends of the pusher and introducer are aligned. As in the previous discussion, the introducer has a tapering interior surface at the distal end which receives a portion of the blood vessel and impedes the distal end from entering said blood vessel. Alternatively, the pusher may have the interior tapering surface. After setting of the depth indicator on the introducer with the dilation pusher in place, the system is then removed from the tissue tract and the dilation pusher is removed from the introducer. The introducer is then prepared for delivery of the pledget by hydrating and staging the pledget within the introducer and the delivery pusher is inserted in the introducer. The introducer is then reintroduced over the guidewire and advanced into the tissue tract to the depth indicated by the depth indicator. In this manner, reliable, accurate, and repeatable placement of the pledget is performed without the use of a separate tract dilator.

According to yet another use, the introducer is inserted to the pledget delivery site through a sheath. In this method, the sheath with a removable dilator positioned inside the sheath is advanced over the guidewire into a tissue tract to establish the location of an arterial puncture site. The removable dilator includes a tapering surface at a distal end for receiving a portion of the blood vessel and impeding the dilator from entering the blood vessel. Once the exterior wall of the vessel has been located by tactile feedback, the dilator is withdrawn leaving the sheath in place. The introducer with prepared pledget and pusher are then inserted into the sheath over the guidewire. The introducer may be locked to the sheath, such as by a luer lock. This will position the distal end of the introducer at the distal end of the sheath in preparation for pledget delivery. The combined sheath and introducer system is used to deposit the pledget in the manner described above.

Among other advantages, the absorbable sponge delivery system permits the delivery of more absorbable sponge material down a smaller tract by hydrating and compressing the absorbable sponge material. The over the wire delivery method ensures that the absorbable sponge pledget is delivered directly over the puncture site and remains in the proper position while hemostasis is achieved. The vessel depth indicator system ensures that the absorbable sponge material is positioned adjacent the exterior of the blood vessel and does not extend into the blood vessel to possibly induce thrombosis.

The absorbable sponge material can be absorbed by the body in a period of time between several days and several months depending on the absorbable sponge material used. However, the pledget material may be engineered to provide different rates of absorption. Preferably, the pledget 40 is designed to be absorbed in less than one month.

Although the tract dilator and introducer are primarily intended for delivery of absorbable sponge, non-absorbable sponge may also be delivered with the devices, systems, and methods. A non-absorbable sponge may be desirable where it will be necessary to locate the blood vessel puncture after the procedure.

While an amorphous or discontinuous sponge structure may be used in the present invention, a continuous structure of the delivered absorbable sponge pledget 40 provides more secure and reliable placement of a plug of material against the blood vessel puncture than a paste or liquid. The continuous sponge structure can even facilitate partial withdrawal, removal, or movement of the ejected pledget.

The absorbable sponge material can be hydrated with a clotting agent such as thrombin, a contrast agent, another beneficial agent, a combination of agents, or the like. Alternatively, the pledget material itself may contain an agent such as a clotting agent, a contrast agent, another beneficial agent, a combination of agents, or the like.

The absorbable sponge pledget may be presoaked with a beneficial agent such as thrombin for delivery of the beneficial agent to the punctured blood vessel. Alternatively, the pledget may be hydrated with a beneficial liquid agent used as the hydrating fluid within the syringe 50. Further, the beneficial agent may be delivered to the pledget after the pledget is ejected at the blood vessel puncture site through the lumen of the pusher 14 or through the introducer 12.

The treatment of a blood vessel puncture with a hydrated and injected pledget 40 of absorbable sponge to facilitate hemostasis provides substantial advantages in comfort over external pressure methods. In addition, the present invention also provides advantages over the insertion of an absorbable sponge material in a dry state or injection of a liquid or paste. In particular, the hydration and manipulation or "kneading" of the hydrated Gelfoam™ pledget 40 as it is passed through the introducer 12 improves the expansion and absorption characteristics of the Gelfoam™. The injected Gelfoam™ conforms in shape quickly to the shape of the puncture site and immediately begins blocking blood flow through the puncture site and providing local compression. In contrast, a dry piece of sponge material does not swell until the blood has sufficiently saturated the sponge material, which can take up to hours. The hydrated and kneaded sponge material will expand to a larger size much more quickly when wetted than a piece of dry sponge material when wetted.

Because the amount of subcutaneous fat and tissue between the epidermal layer 106 and the blood vessel 102 varies between patients from approximately 0.5 cm to 15 cm or more, the system may be provided in different lengths for use in different patients. The pledget 40 size and shape may also be varied for different patients. The absorbable sponge material should form a complete plug over the puncture site without expanding into the blood vessel or exiting the skin of the patient. In some instances where the amount of subcutaneous tissue is great it may be desirable to deliver multiple pledgets 40 in spaced apart positions along the tract leading to the puncture site.

The particular size and shape of the tract dilator 10 may vary depending on the size of the access site, amount of subcutaneous tissue, and the size of pledget 40 to be delivered. The particular length of the tract dilator 10 depends on the subcutaneous tissue depth of the patient.

The invention also includes several embodiments of methods of using a device for determining the depth of an incision that extends from the epidermal layer to a blood vessel. The method as illustrated in FIGS. 6 and 7, comprises the steps of introducing an elongated member 32 through an incision, the elongated member having a proximal end 22, and a distal end 20 configured for locating a blood vessel 66 while impending the distal end of the elongated member from entering the blood vessel, locating the blood vessel by receiving a portion of a wall of the blood vessel with the distal end. Once the wall of the blood vessel 66 has been located the operator sets a depth indicating member 30 to mark a depth of the blood vessel 66.

In another embodiment of the method, the elongated member 32 is introduced over a guidewire 26 into a tissue tract. The guidewire 26 has a preselected stiffness to raise a portion of an anterior proximal lip 62 of a blood vessel 66 adjacent to a blood vessel puncture 64. The elongated member 32 is introduced until an elastic recoil is introduced on the blood vessel 66. The elastic recoil is felt by the operator of the elongated member 32 as the distal end 20 catches the anterior proximal lip 62 of the puncture site 64.

The guidewire 26 directs the wall of the blood vessel 66 to be received by the elongated member 32. The diameter of the elongated member 32 is larger than the diameter of the puncture of the blood vessel 66. The guidewire 26 pushes the anterior proximal lip 62 into the interior surface of the elongated member 32. The force vector generated by the anterior proximal lip 62 on the elongated member 32 represents the elastic recoil used to identify the location of the artery and puncture site 64.

In another embodiment, the elongated member 32 can be introduced to determine a depth of the incision before the placement of a procedural sheath and before an intervascular procedure has been performed. Alternatively, the elongated member 32 can be introduced after the placement of a procedural sheath and after a procedure has been completed, or after removal of the procedural sheath.

In another embodiment, the depth of the incision can be determined by inserting a portion of an extending control member 472 into the blood vessel, wherein the extending control member at least partially occludes the puncture in the blood vessel wall. Fluid from the blood vessel will enter the extending control member 472, and the fluid from the blood vessel becomes visible to communicate with the operator by providing visual feedback to the operator.

While the invention has been described in detail with reference to the preferred embodiments thereof, it will be apparent to one skilled in the art that various changes and modifications can be made and equivalents employed, without departing from the present invention.

What is claimed is:

1. A device for determining a depth of incision that extends from an epidermal layer to a blood vessel having a puncture, the device comprising:
   an elongated member including a distal end and a proximal end;
   a lumen extending through the elongated member, the lumen having a proximal end coincident with the elongated member proximal end and a distal end spaced proximally from the elongated member distal end, the lumen accommodating at least one extending member that enters the blood vessel through the puncture, and
   a tapered surface extending between the elongated member distal end and the lumen distal end, the tapered surface having a larger diameter at the elongated member distal end and a smaller diameter at the lumen distal end, the tapered surface receiving a portion of the blood vessel surrounding the puncture for impeding the distal end of the elongated member from entering the blood vessel.

2. The device according to claim 1, wherein the elongated member has a constant outer diameter.

3. The device according to claim 1, wherein the elongated member has an outer diameter which progressively decreases to a smaller outer diameter at the distal end.

4. The device according to claim 1, wherein the lumen is centered within the elongated member.

5. The device according to claim 1, wherein the lumen is off-center along the longitudinal axis of the elongated member.

6. The device according to claim 1, wherein the tapered surface has a substantially conic shape.

7. The device according to claim 1, wherein the tapered surface has a substantially concave spherical shape.

8. The device according to claim 1, wherein the tapered surface has a substantially stepped configuration.

9. The device according to claim 1, wherein a diameter of the tapered surface at the distal end of the elongated member is about 50% to 99% of an outer diameter of an exterior surface of the elongated member.

10. The device according to claim 1, wherein the tapered surface at the elongated member distal end has a diameter of about 050 to 160 inches.

11. The device according to claim 1, wherein the elongated member comprises a material with a hardness of at least 50 D.

12. The device according to claim 1, wherein a portion of the elongated member comprises a friction reducing material.

13. The device according to claim 1, wherein the elongated member comprises a friction reducing material.

14. The device according to claim 1, further comprising a depth indicating member positioned on an exterior of the elongated member and movable in an axial direction with respect to the elongated member.

15. The device according to claim 14, wherein the depth indicating member is an elastic ring.

16. The device according to claim 1, where the extending member extends beyond the distal end of the elongated member.

17. The device according to claim 16, wherein the extending member includes a proximal end, a distal end, and a lumen which extends from the proximal end to the distal end.

18. The device according to claim 17, wherein the extending member is configured to occlude and control a puncture in the blood vessel.

19. The device according to claim 17, wherein the distal end of the extending member has at least one vent hole for allowing a fluid to enter the lumen of the extending member.

20. The device according to claim 17, wherein the lumen of the extending member tapers from a first diameter at the proximal end to a second smaller diameter at the distal end.

21. The device according to claim 17, wherein the extending member extends from the tapered surface of the device by about 10 to 6 inches.

22. The device according to claim 17, wherein the extending member is formed from a flexible material to prevent the extending member from catching on subcutaneous tissue as the extending member advances through the patient's skin and tissue at the puncture site.

23. A device for determining a depth of an incision that extends from an epidermal layer to a blood vessel puncture site, the device comprising:
    an elongated member having a distal end, a proximal end, and a lumen extending between the proximal and distal ends, the lumen accommodating at least one control member that enters the blood vessel, the distal end including a tapered surface for locating the blood vessel puncture site by capturing an edge of the blood vessel puncture and for impeding entry of the distal end of the elongated member into the vessel; and
    the control member extending from the distal end of the elongated member and configured to be received through the puncture site.

24. The device according to claim 23, further comprising a vent provided in the control member for venting fluid from the control member to the proximal end of the elongated member to provide an indication of location of the control member in the blood vessel.

25. The device according to claim 23, wherein control member is tapered.

26. The device according to claim 23, wherein the control member has a tapered lumen.

27. A method for determining a depth of an incision that extends from an epidermal layer to a puncture in a blood vessel, the method comprising:
    providing an elongated member including a distal end and a proximal end, a lumen extending through the elongated member and having a proximal end coincident with the elongated member proximal end and a distal end spaced proximally from the elongated member distal end, and a tapered surface extending between the elongated member distal end and the lumen distal end, the tapered surface having a larger diameter at the elongated member distal end and a smaller diameter at the lumen distal end;
    introducing the elongated member through the incision; and
    locating the puncture in the blood vessel by receiving a portion of a wall of the blood vessel with the tapered surface.

28. The method for determining a depth of an incision according to claim 27, wherein the elongated member is introduced over a guidewire into a tissue tract.

29. The method for determining a depth of an incision according to claim 28, wherein the guidewire has a preselected stiffness to raise a portion of the wall of the blood vessel adjacent to the puncture.

30. The method for determining a depth of an incision according to claim 28, wherein the guidewire directs the wall of the blood vessel to be received by the elongated member.

31. The method for determining a depth of an incision according to claim 27, wherein the elongated member is introduced until an elastic recoil is produced by the blood vessel.

32. The method for determining a depth of an incision according to claim 31, wherein the elastic recoil is felt by the operator of the elongated member.

33. The method for determining a depth of an incision according to claim 27, wherein the tapered surface is configured to catch an anterior proximal lip of the puncture site.

34. The method for determining a depth of an incision according to claim 27, wherein an outer diameter of the elongated member is larger than a diameter of the puncture of the blood vessel.

35. The method for determining a depth of an incision according to claim 27, wherein a depth indicating member which is slidably movable in a longitudinal direction on the elongated member is set to mark a depth of the puncture in the blood vessel.

36. The method for determining a depth of an incision according to claim 27, further comprising a step of inserting a portion of an extending member into the blood vessel.

37. The method for determining a depth of an incision according to claim 36, wherein the extending member at least partially occludes the puncture in the blood vessel wall.

38. The method for determining a depth of an incision according to claim 36, wherein a fluid from the blood vessel enters the extending member.

39. The method for determining a depth of an incision according to claim 38, wherein the fluid from the blood vessel entering the extending member provides visual feedback to the operator.

40. A method for determining a depth of an incision that extends from an epidermal layer to a puncture in a blood vessel, the method comprising the steps of:
    introducing an elongated member through the incision, the elongated member comprising a distal end and a proximal end, a lumen extending through the elongated member and having a proximal end coincident with the elongated member proximal end and a distal end spaced proximally from the elongated member distal end, the lumen accommodating at least one control member that enters the puncture in the blood vessel, and a tapered surface extending between the elongated member distal end and the lumen distal end, the tapered surface having a larger diameter at the elongated member distal end and a smaller diameter at the lumen distal end;
    providing visual feedback of a general location of the blood vessel puncture by venting blood through the elongated member; and
    providing specific tactile feedback of a specific location of the blood vessel puncture by receiving an edge of the blood vessel surrounding the puncture in the tapered surface of the distal end of the elongated member which impedes entry of the elongated member through the puncture.

41. The method of claim 40, wherein the visual feedback is provided by the control member at the distal end of the elongated member, the control member having a vent hole.

* * * * *

UNITED STATES PATENT AND TRADEMARK OFFICE
CERTIFICATE OF CORRECTION

PATENT NO. : 7,201,725 B1
APPLICATION NO. : 10/069107
DATED : April 10, 2007
INVENTOR(S) : Cragg et al.

It is certified that error appears in the above-identified patent and that said Letters Patent is hereby corrected as shown below:

On page 3, under Other Publications:

Please remove:

"Schievink, et al. The new england journal of medicaine; review articles; intracanial aneurysms; Jan. 2, 1997.

Szikora, et al. Combined Use of stents and cells to treat experimental wide-necked carotid anueryms: Preliminary results; AJNR AM newradiol 15: 1091-1102, Jun. 94.

Turjman, et al. Combined stent implantation & endosacular coil placement for tretment of experimental wide-necked aneurysms:AJNRAM J. Neuroradio 15: 1087-1090 Jun. 94."

And replace it with:

-- Schievink, et al The New England Journal of Medicine; review articles; Intracranial Aneurysms; Jan. 2, 1997

Szikora, et al. Combined use of stents and cells to treat experimental wide-necked carotid anueryms: Preliminary results; AJNR 15: 1091-1102, Jun. 94.

Turjman, et al. Combined stent implantation & endosacular coil placement for treatment of experimental wide-necked aneurysms:AJNRAM J. Neuroradio 15: 1087-1090 Jun. 94. --

UNITED STATES PATENT AND TRADEMARK OFFICE
CERTIFICATE OF CORRECTION

PATENT NO. : 7,201,725 B1
APPLICATION NO. : 10/069107
DATED : April 10, 2007
INVENTOR(S) : Cragg et al.

It is certified that error appears in the above-identified patent and that said Letters Patent is hereby corrected as shown below:

In claim 10, column 14, line 46 please delete "050 to 160" and replace with -- .050 to .160 --.

In claim 21, column 15, line 12 please delete "10" and replace with -- .10 --.

Signed and Sealed this

Tenth Day of June, 2008

JON W. DUDAS
*Director of the United States Patent and Trademark Office*